United States Patent
Wang et al.

(10) Patent No.: US 10,307,237 B2
(45) Date of Patent: Jun. 4, 2019

(54) TISSUE MATRICES AND METHODS OF TREATMENT

(71) Applicant: LifeCell Corporation, Branchburg, NJ (US)

(72) Inventors: Kai-Roy Wang, Jersey City, NJ (US); Sangwook Park, Dunellen, NJ (US); Aaron Barere, Hoboken, NJ (US)

(73) Assignee: LifeCell Corporation, Madison, NJ (US)

( * ) Notice: Subject to any disclaimer, the term of this patent is extended or adjusted under 35 U.S.C. 154(b) by 0 days.

(21) Appl. No.: 15/139,458

(22) Filed: Apr. 27, 2016

(65) Prior Publication Data
US 2016/0331504 A1    Nov. 17, 2016

Related U.S. Application Data

(60) Provisional application No. 62/161,971, filed on May 15, 2015.

(51) Int. Cl.
| | |
|---|---|
| *A61F 2/12* | (2006.01) |
| *A61F 2/00* | (2006.01) |
| *A61B 90/00* | (2016.01) |
| *A61L 27/36* | (2006.01) |

(52) U.S. Cl.
CPC ............ *A61F 2/0063* (2013.01); *A61B 90/02* (2016.02); *A61F 2/12* (2013.01); *A61L 27/3666* (2013.01); *A61F 2002/0068* (2013.01); *A61F 2220/0008* (2013.01); *A61F 2220/0075* (2013.01); *A61L 2430/04* (2013.01)

(58) Field of Classification Search
CPC .. A61F 2/12; A61F 2/0063; A61F 2002/0068; A61F 2220/0008; A61B 2017/00792; A61B 2017/00796
See application file for complete search history.

(56) References Cited

U.S. PATENT DOCUMENTS

| | | |
|---|---|---|
| 3,683,424 A | 8/1972 | Pangman |
| 3,744,094 A | 7/1973 | Bach |
| 4,298,998 A | 11/1981 | Naficy |

(Continued)

FOREIGN PATENT DOCUMENTS

| | | |
|---|---|---|
| CN | 1953657 | 4/2007 |
| CN | 103393482 | 11/2013 |

(Continued)

OTHER PUBLICATIONS

International Search Report and Written Opinion for PCT/US2016/029411 dated Jul. 7, 2016.

(Continued)

*Primary Examiner* — Seema Mathew
(74) *Attorney, Agent, or Firm* — McCarter & English, LLP

(57) ABSTRACT

Methods, systems, and compositions for treatment are provided. The methods can be used to stretch and completely or nearly completely wrap a composition around an implant or tissue expander. The systems can be used to protect an implant or tissue expander by completely or nearly completely wrapping a composition around the implant or tissue expander. The compositions can be used to completely or nearly completely wrap around an implant or tissue expander to provide support and protection to the implant or tissue expander.

14 Claims, 11 Drawing Sheets

(56) References Cited

U.S. PATENT DOCUMENTS

| | | | |
|---|---|---|---|
| 4,840,629 A | 6/1989 | Bustos | |
| 4,936,858 A | 6/1990 | O'Keeffe | |
| 5,066,303 A | 11/1991 | Bark et al. | |
| 5,352,307 A | 10/1994 | Wild | |
| 5,356,429 A | 10/1994 | Seare | |
| 5,447,535 A | 9/1995 | Muller | |
| 5,584,884 A | 12/1996 | Pignataro | |
| 5,658,328 A | 8/1997 | Johnson | |
| 5,658,330 A | 8/1997 | Carlisle et al. | |
| 5,676,161 A * | 10/1997 | Breiner | A61B 17/32053 |
| | | | 128/898 |
| 5,713,959 A | 2/1998 | Bartlett et al. | |
| 5,733,337 A | 3/1998 | Carr, Jr. et al. | |
| 5,755,791 A | 5/1998 | Whitson et al. | |
| 5,954,767 A | 9/1999 | Pajotin et al. | |
| 5,968,096 A | 10/1999 | Whitson et al. | |
| 5,997,575 A | 12/1999 | Whitson et al. | |
| 6,099,566 A | 8/2000 | Vonderharr et al. | |
| 6,203,570 B1 | 3/2001 | Baeke | |
| 6,210,439 B1 * | 4/2001 | Firmin | A61F 2/0059 |
| | | | 606/151 |
| 6,368,541 B1 | 4/2002 | Pajotin et al. | |
| 6,638,308 B2 | 10/2003 | Corbitt, Jr. et al. | |
| 6,666,892 B2 | 12/2003 | Hiles et al. | |
| 6,723,133 B1 | 4/2004 | Pajotin | |
| 6,736,823 B2 | 5/2004 | Darois et al. | |
| 6,736,854 B2 | 5/2004 | Vadurro et al. | |
| 6,740,122 B1 | 5/2004 | Pajotin | |
| 6,802,861 B1 | 10/2004 | Hamas | |
| 7,011,688 B2 | 3/2006 | Gryska et al. | |
| 7,081,135 B2 | 7/2006 | Smith et al. | |
| 7,476,249 B2 * | 1/2009 | Frank | A61F 2/12 |
| | | | 623/8 |
| 7,658,727 B1 | 2/2010 | Fernandes et al. | |
| 7,699,895 B2 | 4/2010 | Hiles et al. | |
| 7,875,074 B2 | 1/2011 | Chen et al. | |
| 7,901,346 B2 * | 3/2011 | Kovac | A61F 2/0045 |
| | | | 600/37 |
| 8,007,531 B2 | 8/2011 | Frank | |
| 8,128,708 B2 | 3/2012 | Hiles et al. | |
| 8,147,546 B2 | 4/2012 | Stone et al. | |
| 8,313,527 B2 | 11/2012 | Powell | |
| 8,323,352 B2 | 12/2012 | Friedman et al. | |
| 8,357,172 B2 | 1/2013 | Harper et al. | |
| 8,487,012 B2 | 7/2013 | Goraltchouk | |
| 8,597,173 B2 * | 12/2013 | O'Hern | A61B 17/0401 |
| | | | 600/37 |
| 8,685,296 B2 | 4/2014 | Liu et al. | |
| 8,858,647 B2 | 10/2014 | Markman | |
| 8,876,899 B2 | 11/2014 | Maxwell | |
| 8,905,914 B2 | 12/2014 | Beckman et al. | |
| 8,986,377 B2 | 3/2015 | Richter et al. | |
| 9,101,458 B2 | 8/2015 | Sun et al. | |
| 9,351,819 B2 | 5/2016 | Harper et al. | |
| 9,510,937 B2 | 12/2016 | Sun et al. | |
| 9,549,812 B2 | 1/2017 | Shetty et al. | |
| 2001/0041936 A1 | 11/2001 | Corbitt, Jr. et al. | |
| 2002/0103542 A1 | 8/2002 | Bilbo | |
| 2002/0147461 A1 | 10/2002 | Aldrich et al. | |
| 2003/0130747 A1 | 7/2003 | Abraham et al. | |
| 2003/0143207 A1 | 7/2003 | Livesey et al. | |
| 2003/0212461 A1 | 11/2003 | Vadurro et al. | |
| 2003/0212462 A1 | 11/2003 | Gryska et al. | |
| 2004/0049269 A1 | 3/2004 | Corbitt, Jr. et al. | |
| 2004/0260315 A1 | 12/2004 | Dell et al. | |
| 2005/0021141 A1 | 1/2005 | Bleyer et al. | |
| 2005/0165425 A1 | 7/2005 | Croce et al. | |
| 2005/0187624 A1 | 8/2005 | Corbitt, Jr. | |
| 2005/0250977 A1 | 11/2005 | Montpetit et al. | |
| 2005/0260176 A1 | 11/2005 | Ayares et al. | |
| 2006/0030939 A1 | 2/2006 | Frank | |
| 2006/0167338 A1 | 7/2006 | Shafaram | |
| 2006/0264948 A1 * | 11/2006 | Williams | A61B 17/70 |
| | | | 606/71 |
| 2007/0038299 A1 | 2/2007 | Stone et al. | |
| 2007/0088434 A1 * | 4/2007 | Frank | A61F 2/12 |
| | | | 623/8 |
| 2007/0116678 A1 | 5/2007 | Sung et al. | |
| 2007/0250177 A1 | 10/2007 | Bilbo | |
| 2008/0027273 A1 | 1/2008 | Gutterman | |
| 2008/0082113 A1 | 4/2008 | Bishop et al. | |
| 2008/0097601 A1 | 4/2008 | Codori-Hurff et al. | |
| 2008/0108134 A1 | 5/2008 | Murphy et al. | |
| 2008/0167729 A1 | 7/2008 | Nelson et al. | |
| 2008/0260853 A1 | 10/2008 | Firestone | |
| 2008/0281418 A1 | 11/2008 | Firestone | |
| 2008/0281419 A1 | 11/2008 | Matheny et al. | |
| 2009/0024227 A1 | 1/2009 | Lesh | |
| 2009/0024228 A1 | 1/2009 | Lesh | |
| 2009/0082864 A1 | 3/2009 | Chen | |
| 2009/0125107 A1 | 5/2009 | Maxwell | |
| 2009/0198332 A1 | 8/2009 | Becker | |
| 2009/0216338 A1 | 8/2009 | Gingras et al. | |
| 2009/0240102 A1 * | 9/2009 | Rane | A61B 17/06109 |
| | | | 600/37 |
| 2009/0240342 A1 | 9/2009 | Lindh et al. | |
| 2010/0003306 A1 | 1/2010 | Von Waldburg-Zeil | |
| 2010/0010627 A1 | 1/2010 | Matheny | |
| 2010/0023029 A1 | 1/2010 | Young | |
| 2010/0028396 A1 | 2/2010 | Ward et al. | |
| 2010/0152530 A1 * | 6/2010 | Timmer | A61F 2/0045 |
| | | | 600/37 |
| 2010/0191330 A1 | 7/2010 | Lauryssen et al. | |
| 2010/0217388 A1 | 8/2010 | Cohen et al. | |
| 2010/0226960 A1 | 9/2010 | Chudzik et al. | |
| 2011/0035004 A1 | 2/2011 | Maxwell | |
| 2011/0054588 A1 | 3/2011 | Xu et al. | |
| 2011/0177150 A1 | 7/2011 | Pathak et al. | |
| 2011/0190573 A1 * | 8/2011 | Deegan | D04B 21/16 |
| | | | 600/37 |
| 2011/0276039 A1 | 11/2011 | Markman | |
| 2012/0052040 A1 | 3/2012 | Hunter et al. | |
| 2012/0059411 A1 | 3/2012 | Sun et al. | |
| 2012/0158134 A1 | 6/2012 | Codori-Hurff et al. | |
| 2012/0165957 A1 * | 6/2012 | Everland | A61F 2/0045 |
| | | | 623/23.72 |
| 2013/0053956 A1 | 2/2013 | Powell | |
| 2013/0085579 A1 | 4/2013 | Markman | |
| 2014/0039617 A1 * | 2/2014 | Maxwell | A61F 2/12 |
| | | | 623/8 |
| 2014/0276997 A1 * | 9/2014 | Harrah | A61L 31/129 |
| | | | 606/151 |
| 2015/0012089 A1 * | 1/2015 | Shetty | A61F 2/0077 |
| | | | 623/8 |
| 2015/0112434 A1 * | 4/2015 | Felix | A61L 31/148 |
| | | | 623/8 |
| 2015/0150674 A1 * | 6/2015 | Ansorge | A61F 2/12 |
| | | | 623/8 |
| 2015/0157451 A1 | 6/2015 | Bowley et al. | |
| 2015/0223928 A1 | 8/2015 | Limem et al. | |
| 2015/0359622 A1 | 12/2015 | Matheny | |
| 2015/0359933 A1 | 12/2015 | Matheny | |
| 2016/0045198 A1 | 2/2016 | Bachrach et al. | |
| 2016/0151062 A1 | 6/2016 | Bachrach et al. | |
| 2016/0242890 A1 | 8/2016 | Harper et al. | |
| 2017/0007394 A1 | 1/2017 | Shetty et al. | |
| 2017/0071723 A1 | 3/2017 | Sun et al. | |
| 2017/0181841 A1 * | 6/2017 | Weinzweig | A61F 2/12 |
| 2017/0216018 A1 * | 8/2017 | Limem | A61F 2/12 |

FOREIGN PATENT DOCUMENTS

| | | |
|---|---|---|
| DE | 102006029605 A1 | 12/2007 |
| EP | 0338701 | 10/1989 |
| FR | 2447182 | 8/1980 |
| JP | 09-047503 | 2/1997 |
| JP | 10-158906 | 6/1998 |
| JP | 2005-536228 | 12/2005 |
| WO | WO 2003/068118 | 8/2003 |
| WO | WO 2003/084410 | 10/2003 |
| WO | WO 2004/096098 | 11/2004 |
| WO | WO 2005/089411 | 3/2005 |

(56) References Cited

FOREIGN PATENT DOCUMENTS

| WO | WO 2006/115892 | 11/2006 |
|---|---|---|
| WO | WO 2006/135998 | 12/2006 |
| WO | WO 2007/004214 | 1/2007 |
| WO | WO 2007/134134 | 5/2007 |
| WO | WO 2007/131110 | 11/2007 |
| WO | WO 2008/016919 | 2/2008 |
| WO | WO 2008/067317 | 6/2008 |
| WO | WO 2008/121816 | 10/2008 |
| WO | WO 2009/001293 | 12/2008 |
| WO | WO 2009/065013 | 5/2009 |
| WO | WO 2009/114052 | 9/2009 |
| WO | WO 2010/041101 | 4/2010 |
| WO | WO 2014/041577 | 3/2014 |
| WO | WO 2015/065923 | 5/2015 |
| WO | PCT/US2016/029411 | 4/2016 |

OTHER PUBLICATIONS

Berna, G. et al., "Evaluation of a Novel Breast Reconstruction Technique Using the Braxon® Acellular Dermal Matrix: A New Muscle-Sparing Breast Reconstruction", *ANZ J. Surg.* (Sep. 29, 2014).

Badylak et al., "Extracellular Matrix as a Biological Scaffold Material: Structure and Function," *Acta Biomaterialia* (2009).

Pope, Eric R., "Mesh Skin Grafting", Veterinary Clinics of North America: Small Animal Practice, vol. 20, No. 1, pp. 177-187 (Jan. 1990).

Goes, Joao C.S., "Periareolar Mammaplasty: Double Skin Technique with Application of Polygractine 910 Mesh", Rev. Soc. Bras. Cir. Plast. Estet. Reconstr., 7(1, 2, 3) (1992).

Goes, Joao C.S., "Periareolar Mammaplasty: Double Skin Technique with Application of Polyglactine or Mixed Mesh", Plastic and Reconstructive Surgery (Apr. 1996).

Goes, Joao C.S., "Periareolar Mammaplasty With Mixed Mesh Support: The Double Skin Technique", Operative Techniques in Plastic and Reconstructive Surgery, vol. 3, No. 3, pp. 199-206 (Aug. 1996).

Goes, Joao C.S., "Periareolar Mastopexy and Reduction with Mesh Support, Double Skin Technique", Surgery of the Breast: Principles and Art, 697 (1998).

Goes, Joao C.S., "Periareolar Mastopexy: Double Skin Technique with Mesh Support", Aesthetic Surgery Journal, (Mar./Apr. 2003).

Baxter, R.A., "Intracapsular Allogenic Dermal Grafts for Breast Implant-Related Problems", Plast. Reconstr. Surg., 112(6): 1692-1696 (2003).

Goes, Joao C.S. et al., "The Application of Mesh Support in Periareolar Breast Surgery: Clinical and Mammographic Evaluation", Aesth. Plast. Surg., 28:268-274 (2004).

Breuing, K.H. et al., "Immediate Bilateral Breast Reconstruction With Implants and Inferolateral AlloDerm Slings", Annals of Plastic Surgery, 55(3): 232-239 (2005).

Breuing, K.H. et al., "Inferolateral AlloDerm Hammock for Implant Coverage in Breast Cadaveric Dermal Slings", Annals of Plastic Surgery, 59(3): 250-255 (2007).

Bindingnavele et al., "Use of acellular cadaveric dermis and tissue expansion in postmastectomy breast reconstruction", Journal of Plastic, Reconstructive, and Aesthetic Surgery, 60(2007): 1214-1218.

Colwell, A.S. et al., "Improving Shape and Symmetry in Mastopexy With Autologous or Cadaveric Dermal Slings", Annals of Plastic Surgery, 61(2): 138-142 (2008).

Darcy, C.M., "A Technique for Preparing Meshed Skin Grafts With Planned Expansion Ratios", British Journal of Plastic Surgery, 56(1): 77-79 (2003).

Duncan, D.I., "Correction of Implant Rippling Using Allograft Dermis", Aesthetic Surgery Journal, 21(1): 81-84 (2001).

Gamboa-Bobadilla, G.M., "Implant Breast Reconstruction using Acellular Dermal Matrix", Annals of Plastic Surgery, 56(1): 22-25 (2006).

Salzberg, C.A., "Nonexpansive Immediate Breast Reconstruction using Human Acellular Tissue Matrix Graft (AlloDerm)", Annals of Plastic Surgery, 57(1): 1-5 (2006).

Topol, B.M. et al., "Immediate Single-Stage Breast Reconstruction using Implants and Human Acellular Dermal Tissue Matrix With Adjustment of the Lower Pole of the Breast to Reduce Unwanted Lift", Annals of Plastic Surgery, 61(5): 494-499 (2008).

Zienowicz, R.J. et al., "Implant-Based Breast Reconstruction With Allograft", Plast. Reconstr. Surg., 120: 373-374 (2007).

Xu, Hui et al., "A Porcine-Derived Acellular Dermal Scaffold that Supports Soft Tissue Regeneration: Removal of Terminal Galactose-$\alpha$-(1,3)-Galactose and Retention of Matrix Structure," Tissue Engineering, vol. 15, 1-13 (2009).

\* cited by examiner

TISSUE MATRICES AND METHODS OF TREATMENT

This application claims the benefit under 35 USC § 119 of commonly assigned U.S. Provisional Patent Application No. 62/161,971, filed on May 15, 2015. The entire content of the foregoing provisional patent application is incorporated herein by reference.

The present disclosure relates to methods of treatment, and more particularly, to methods of treatment and compositions and systems for treatment in accordance with the methods.

Various methods are used for breast augmentation or reconstruction. One method involves sub-glandular placement of breast implants or tissue expanders, a procedure that is generally considered less complicated compared to other techniques because the pectoral muscles are left intact, resulting in shorter operation times, lower pain levels, and shorter recovery times. However, placing breast implants or tissue expanders in a sub-glandular palpability of the implant, superficial ripples, and a potential for capsular contracture.

Rippling can occur in patients with inadequate breast tissue for covering the implant or tissue expander, resulting in folds or wrinkles in the implant or tissue expander that are visible through the skin. In particular, since the implant or tissue expander is placed over the pectoral muscles, there may be inadequate breast tissue to cover the implant or tissue expander. Rippling is typically most noticeable on the bottom or sides of the implant or tissue expander, but may also occur in the middle near the cleavage.

Capsular contracture can occur as a response of the immune system to foreign materials in the human body. In particular, capsular contracture involves the formation of capsules of tightly woven collagen fibers created by the immune response to the presence of foreign objects, such as implants or tissue expanders, in the body. The collagen-fiber capsule tightens and squeezes the breast implant or tissue expander, resulting in pain and discomfort to the patient, as well s a distortion of the breast implant or tissue expander.

Various products are used as protective sleeves to completely surround the breast implant or tissue expander prior to sub-glandular implantation. For example, some products are formed from completely solid sheets of acellular dermal matrix (ADM) that are trimmed to conform to the size of and wrap around the breast implant or tissue expander, and are sutured around the breast implant or tissue expander. Berna, G. et al., "Evaluation of A Novel Breast Reconstruction Technique Using the Braxon® Acellular Dermal Matrix: A New Muscle-Sparing Breast Reconstruction", *ANZ J. Surg.* (Sep. 29, 2014), doi: 10.1111/ans.12849. Such products, however, cover the entire surface of the implant or tissue expander, and therefore require a substantial amount of tissue, resulting in an expensive product. Further, trimming the excess tissue to conform to the size of the breast implant or tissue expander results in a waste of tissue.

To cover an implant or tissue expander, it may be desirable to use a composition that has one or more mesh patterns that facilitate stretching and expanding the composition to completely or nearly completely wrap around the implant or tissue expander, while providing the necessary coverage and support to the implant or tissue expander. Accordingly, methods of treatment including compositions, as well as compositions and systems used in the methods, are provided.

According to certain embodiments, a method of treatment is provided. The method can include providing a composition. The composition can include a tissue matrix or synthetic material defining a composition body. The composition can include at least one mesh pattern formed in at least a portion of the composition body. The method can include stretching and expanding the composition body at the mesh pattern to completely or nearly completely wrap the composition around or position the composition onto an implant or a tissue expander. The mesh pattern allows less material to be used to form the composition body, while providing the necessary support and/or coverage to the implant or tissue expander with the composition.

In certain embodiments, the tissue matrix can be a tissue matrix sheet defining a planar and flexible configuration. In certain embodiments, the tissue matrix can be an acellular tissue matrix. In certain embodiments, the tissue matrix can be an acellular dermal matrix.

In certain embodiments, the composition can include a central region and four extensions extending from the central region. The method can include forming the mesh pattern in at least one of the four extensions. The method can include forming the mesh pattern in the central region. The method can include interlocking two of the four extensions of the composition with a fastening element. The method can include feeding the fastening element through the mesh pattern and interlocking the fastening element to a strip of material associated with the mesh pattern. In certain embodiments, the method can include interlocking the four extensions of the composition with a fastening element, e.g., a T-shaped fastening element.

In certain embodiments, the composition can include a top region, a central region, and a bottom region. The composition can include a first flap and a second flap extending from opposing sides of the central region. The composition can include at least one strap integrally formed adjacent to an edge of the bottom region. The method can include stretching the at least one strap around a portion of the implant or tissue expander to maintain the composition in a wrapped configuration.

In certain embodiments, the composition can include two flaps extending from one edge of the composition body. The method can include passing the two flaps through slits of the mesh pattern to maintain the composition completely or nearly completely wrapped around the implant or tissue expander.

In certain embodiments, the composition can include a first composition half and a second composition half. The first composition half can include two flaps extending from a top edge and two flaps extending from a bottom edge. The method can include passing the two flaps extending from the top edge of the first composition half into slits of the mesh pattern of one edge of the second composition half. The method can include passing the two flaps extending from the bottom edge of the first composition half into slits of the mesh pattern of an opposing edge of the second composition half. Interlocking the flaps with the slits of the mesh pattern maintains the composition completely or nearly completely wrapped around the implant or tissue expander.

According to certain embodiments, a composition for treatment is provided. The composition can include a composition body and a mesh pattern formed in at least a portion of the composition body. The composition body can be formed from a tissue matrix or synthetic material. The composition body can be configured to stretch and expand at the mesh pattern to completely or nearly completely wrap the composition body around or position the composition body onto an implant or tissue expander.

In certain embodiments, the tissue matrix can be a tissue matrix sheet defining a planar and flexible configuration. In certain embodiments, the tissue matrix can be an acellular tissue matrix. In certain embodiments, the tissue matrix can be an acellular dermal matrix.

In certain embodiments, the composition body can include a central region and four extensions extending from the central region. At least one of the four extensions can include the mesh pattern formed therein. The central region can include the mesh pattern formed therein. The composition can include a fastening element configured to interlock at least two of the four extensions relative to each other (e.g., two opposing extensions). In certain embodiments, the fastening element can include a linear elongated body. In certain embodiments, the fastening element can define a T-shape.

In certain embodiments, the composition body can include a top region, a central region, and a bottom region. The composition can include a first flap and a second flap extending from opposing sides of the central region. The composition can include at least one strap integrally formed adjacent to an edge of the bottom region. The at least one strap can be configured to stretch around a portion of the implant or tissue expander to maintain the composition body in a wrapped configuration.

In certain embodiments, the composition body can include two flaps extending from one edge of the composition body. The two flaps can be configured to pass through slits of the mesh pattern to maintain the composition body completely or nearly completely wrapped around the implant or tissue expander.

In certain embodiments, the composition body can include a first composition half and a second composition half. The first composition half can include two flaps extending from a top edge and two flaps extending from a bottom edge. In certain embodiments, the first composition half can include two flaps extending from a top edge and the second composition half can include two flaps extending from a bottom edge. The two flaps extending from the top edge of the first composition half can be configured to pass into slits of the mesh pattern of one edge of the second composition half. The two flaps extending from the bottom edge of the first composition half can be configured to pass into slits of the mesh pattern of an opposing edge of the second composition half. Interlocking of the flaps with the mesh pattern maintains the composition completely or nearly completely wrapped around the implant or tissue expander.

According to certain embodiments, a system for treatment is provided. The system can include a composition. The composition can include a tissue matrix or synthetic material defining a composition body. The composition can include a mesh pattern formed in at least a portion of the composition body. The system includes an implant or a tissue expander. The composition body can be configured to stretch and expand at the mesh pattern to completely or nearly completely wrap the composition body around or position the composition body onto the implant or tissue expander.

In certain embodiments, the tissue matrix can be a tissue matrix sheet defining a planar and flexible configuration. In certain embodiments, the tissue matrix can be an acellular tissue matrix. In certain embodiments, the tissue matrix can be an acellular dermal matrix.

In certain embodiments, the composition body can include a central region and four extensions extending from the central region. At least one of the four extensions can include the mesh pattern formed therein. The central region can include the mesh pattern formed therein. The composition can include a fastening element configured to interlock at least two of the four extensions relative to each other (e.g., two opposing extensions). In certain embodiments, the fastening element can include a linear elongated body. In certain embodiments, the fastening element can define a T-shape.

In certain embodiments, the composition body can include a top region, a central region, and a bottom region. The composition can include a first flap and a second flap extending from opposing sides of the central region. The composition can include at least one strap integrally formed adjacent to an edge of the bottom region. The at least one strap can be configured to stretch around a portion of the implant or tissue expander to maintain the composition body in a wrapped configuration.

In certain embodiments, the composition body can include two flaps extending from one edge of the composition body. The two flaps can be configured to pass through slits of the mesh pattern to maintain the composition body completely or nearly completely wrapped around the implant or tissue expander.

In certain embodiments, the composition body can include a first composition half and a second composition half. The first composition half can include two flaps extending from a top edge and two flaps extending from a bottom edge. In certain embodiments, the first composition half can include two flaps extending from a top edge and the second composition half can include two flaps extending from a bottom edge. The two flaps extending from the top edge of the first composition half can be configured to pass into slits of the mesh pattern of one edge of the second composition half. The two flaps extending from the bottom edge of the first composition half can be configured to pass into slits of the mesh pattern of an opposing edge of the second composition half. Interlocking of the flaps with the mesh pattern maintains the composition completely or nearly completely wrapped around the implant or tissue expander.

DESCRIPTION OF CERTAIN EXEMPLARY EMBODIMENTS

Figure 2:
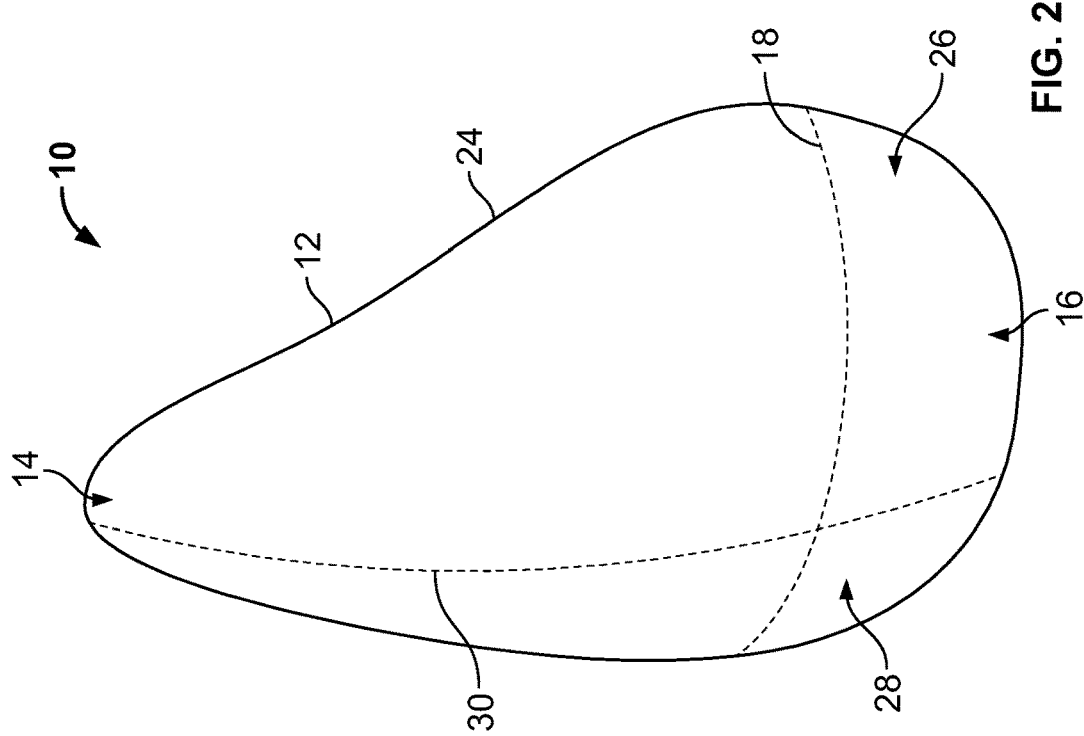
FIG. 2 is a side view of a breast implant or tissue expander, according to certain embodiments.

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Various human and animal tissues can be used to produce products or compositions for treating patients. For example, various tissue products for regeneration, repair, augmentation, reinforcement, and/or treatment of human tissues that have been damaged or lost due to various diseases and/or structural damage (e.g., from trauma, surgery, atrophy, and/or long-term wear and degeneration) have been produced. Such products can include, for example, acellular tissue matrices, tissue allografts or xenografts, and/or reconstituted tissues (i.e., at least partially decellularized tissues that have been seeded with cells to produce viable materials).

In certain embodiments, these products or compositions can be completely or partially decellularized to yield acellular tissue matrices or extracellular tissue materials to be used for patients. For example, various tissues, such as skin, intestine, bone, cartilage, nerve tissue (e.g., nerve fibers or dura), tendons, ligaments, or other tissues can be completely or partially decellularized to produce tissue products useful for patients. In some cases, these decellularized products can be used without addition of exogenous cellular materials (e.g., stem cells). In certain cases, these decellularized products can be seeded with cells from autologous sources or other sources to facilitate treatment. Suitable processes for producing acellular tissue matrices are described below.

Tissue products can be selected to provide a variety of different biological and mechanical properties. For example, an acellular tissue matrix or other tissue product can be selected to allow tissue ingrowth and remodeling to assist in regeneration of tissue normally found at the site where the matrix is implanted. For example, an acellular tissue matrix, when implanted on or into fascia, may be selected to allow regeneration of the fascia without excessive fibrosis or scar formation. In certain embodiments, the tissue product can be formed from ALLODERM® or STRATTICE™, which are human and porcine acellular dermal matrices, respectively. Alternatively, other suitable acellular tissue matrices can be used, as described further below. The methods for shaping tissues having an extracellular matrix can be used to process any collagenous tissue type, and for any tissue matrix product. For example, a number of biological scaffold materials as described by Badylak et al., or any other similar materials, can be used to produce tissues with a stable three-dimensional shape. Badylak et al., "Extracellular Matrix as a Biological Scaffold Material: Structure and Function," *Acta Biomaterialia* (2008), doi:10.1016/j.actbio.2008.09.013. In certain embodiments, the compositions discussed herein can be formed from or can include a tissue product, a synthetic material, or both.

The term "acellular tissue matrix," as used herein, refers generally to any tissue matrix that is substantially free of cells and/or cellular components. Skin, parts of skin (e.g., dermis), and other tissues such as blood vessels, heart valves, fascia, cartilage, bone, and nerve connective tissue may be used to create acellular matrices within the scope of the present disclosure. Acellular tissue matrices can be tested or evaluated to determine if they are substantially free of cell and/or cellular components in a number of ways. For example, processed tissues can be inspected with light microscopy to determine if cells (live or dead) and/or cellular components remain. In addition, certain assays can be used to identify the presence of cells or cellular components. For example, DNA or other nucleic acid assays can be used to quantify remaining nuclear materials within the tissue matrices. Generally, the absence of remaining DNA or other nucleic acids will be indicative of complete decellularization (i.e., removal of cells and/or cellular components). Finally, other assays that identify cell-specific components (e.g., surface antigens) can be used to determine if the tissue matrices are acellular.

In general, the steps involved in the production of an acellular tissue matrix include harvesting the tissue from a donor (e.g., a human cadaver or animal source) and cell removal under conditions that preserve biological and structural function. In certain embodiments, the process includes chemical treatment to stabilize the tissue and avoid biochemical and structural degradation together with or before cell removal. In various embodiments, the stabilizing solution arrests and prevents osmotic, hypoxic, autolytic, and proteolytic degradation, protects against microbial contamination, and reduces mechanical damage that can occur with tissues that contain, for example, smooth muscle components (e.g., blood vessels). The stabilizing solution may contain an appropriate buffer, one or more antioxidants, one or more oncotic agents, one or more antibiotics, one or more protease inhibitors, and/or one or more smooth muscle relaxants.

While an acellular tissue matrix may be made from one or more individuals of the same species as the recipient of the acellular tissue matrix graft, this is not necessarily the case. Thus, for example, an acellular tissue matrix may be made from porcine tissue and implanted in a human patient.

Species that can serve as recipients of acellular tissue matrix and donors of tissues or organs for the production of the acellular tissue matrix include, without limitation, mammals, such as humans, nonhuman primates (e.g., monkeys, baboons, or chimpanzees), pigs, cows, horses, goats, sheep, dogs, cats, rabbits, guinea pigs, gerbils, hamsters, rats, or mice.

The compositions discussed herein can be implemented to cover an implant or tissue expander prior to sub-glandular implantation of the implant or tissue expander to reduce or prevent palpability of ripples and/or capsular contracture. Although discussed herein with respect to sub-glandular reconstruction and augmentation procedures, it should be understood that the disclosed compositions can be implemented for alternative medical procedures involving a variety of implants. Covering the implant or tissue expander with the composition allows for a smoother operation and improved healing by reducing any reactions from implanting a foreign element into the human body.

The compositions can include one or more mesh patterns formed in the composition body that facilitate stretching and expanding of the composition to wrap around the implant or tissue expander, while providing the necessary coverage and support to the implant or tissue expander. In particular, the mesh patterns reduce the amount of tissue or material that must be used to form the composition, thereby reducing the cost of preparing the material.

In addition, the stretchable or expandable property of the composition due to the mesh patterns allows the composition to conform to the size of the implant or tissue expander without the need to trim and discard excess tissue. Smaller amounts of tissue can therefore be used to cover the implant or tissue expander without the need for trimming the composition. As such, the disclosed compositions reduce waste of expensive tissue materials that form the compositions.

In the stretched and expanded configuration, the mesh patterns form perforations through the body of the composition, thereby exposing portions of the implant or tissue expander. However, it is noted that the exposure of the implant or tissue expander through the perforations or openings of the mesh pattern still permits the compositions to provide the necessary coverage to the implant or tissue expander to reduce or prevent undesired reactions between the breast tissue and the implant or tissue expander.

In certain embodiments, the composition can be formed from an acellular dermal matrix (ADM) configured to provide full coverage (e.g., substantially full coverage due to the mesh patterns) to the implant or tissue expander. In certain embodiments, the composition can be formed from a synthetic material. In certain embodiments, the composition can be formed from a combination of ADM and synthetic materials. The composition can provide tissue to camouflage the implant or tissue expander to decrease palpability of ripples, provide a natural tissue barrier between the implant or tissue expander and the breast tissue flap, and shield the implant or tissue expander from puncture during adjust fat transfer or other medical techniques.

The mesh patterns can be designed to optimize coverage of the composition relative to the implant or tissue expander, minimize the total square area of the tissue composition, and maintain beneficial regenerative properties of the tissue composition post-implantation. Because the composition serves as coverage over the implant or tissue expander and a barrier between the host tissue and the implant or tissue expander, the mesh patterns are configured to provide sufficient coverage to both mask the implant or tissue expander, as well as prevent formation of a continuous capsule.

The geometry of the composition can conform to the three-dimensional shape of the breast pocket and tissue expander. In particular, the mesh patterns allow the composition to stretch and expand in the appropriate regions to conform to the geometry of the implant or tissue expander to be positioned into the breast pocket.

Adjunct fat injection techniques are generally used on an upper pole of the breast. Therefore, in certain embodiments, rather than a mesh pattern, a continuous matrix structure can be maintained at the upper pole region of the composition to provide protection from medical devices used during the adjunct fat injection technique.

The compositions can include geometries with fastening elements or features that allow for fixation of the composition to the implant or tissue expander. In certain embodiments, the composition can include one or more flaps that fit into and through the perforations created by the mesh pattern in the composition. In certain embodiments, a single continuous sheet or piece of ADM can be wrapped around the implant or tissue expander and attached to the implant or tissue expander by feeding the flaps into the perforations and fixating the flaps with suture.

In certain embodiments, the composition can include two separate pieces or sheets of ADM, e.g., a first composition half and a second composition half. The first composition half can include one or more mesh patterns, e.g., at the lower pole, and can be configured to cover the posterior portion of the implant or tissue expander. The second composition half can include flaps located on and extending from both upper and lower poles that are designed for passage through the mesh pattern and suture fixation to the meshed areas of the posterior piece, e.g., the first composition half. The second composition half can therefore cover and provide the necessary support to the anterior portion of the implant or tissue expander, while interlocking with the first composition half to maintain the composition wrapped around the implant or tissue expander.

In certain embodiments, the fastening elements in the form of one or more individual tissue straps can be used to connect portions of the composition to maintain the composition wrapped around the implant or tissue expander. In certain embodiments, the tissue straps can be used to connect the meshed portions of the composition. The tissue straps can include a slit or opening on a proximal end and suture holes on a distal end. The distal end of the tissue strap can be snaked or passed through a perforation of the mesh pattern and then through the slit at the proximal end for fixation of one side of the composition. The distal end can further be snaked or passed through a perforation of the mesh pattern on an opposing side of the composition and sutured to the tissue strap through a suture hole.

In certain embodiments, the composition can include one or more continuous tissue straps formed directly in the composition body that are designed to wrap around portions of the implant or tissue expander and/or the composition body to hold the implant or tissue expander in place within the three-dimensional geometry of the composition during the implantation procedure. The tissues traps can therefore maintain the composition wrapped around the implant or tissue expander. The tissue straps can be cut directly into the geometry of the composition and create a fixation mechanism that is continuous with the composition and does not require suturing.

The compositions discussed herein advantageously provide full tissue coverage to an implant or tissue expander that can be implanted, e.g., sub-glandularly, or the like. Fully covering the implant or tissue expander lowers the risk of capsular contracture and provides a soft tissue barrier to mask the implant or tissue expander. The mesh patterns of the compositions decrease costs associated with creating the compositions. The fastening elements of the compositions can increase the ease of performing the implantation procedure due to a reduction in suturing. The compositions therefore improve the sub-glandular reconstruction or augmentation procedure by creating a more predictable, aesthetic and biologic outcome and simplifies the overall implantation procedure.

Figure 1:
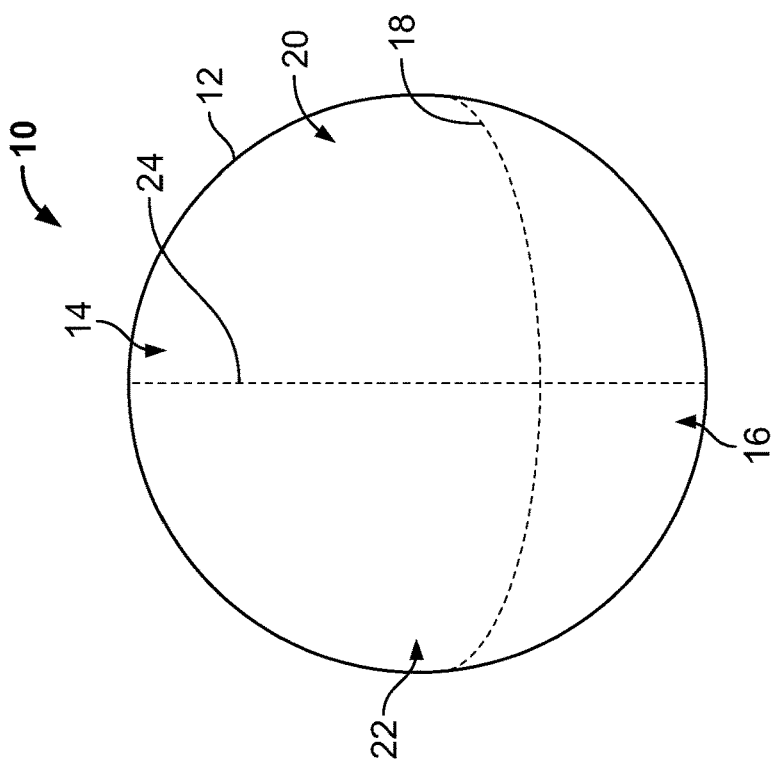
FIG. 1 is front view of a breast implant or tissue expander, according to certain embodiments.

With reference to FIGS. 1 and 2, one embodiment of an implant 10 (e.g., a breast implant or tissue expander) is provided. In certain embodiments, the implant 10 can be any type of breast implant, such as a breast implant including a saline solution, a silicone gel, or a composite filler material. In certain embodiments, the implant 10 can be any type of tissue expander, such as a tissue expander including an inflatable balloon device. In certain embodiments, the implant 10 can be any type of implant and should not be limited to breast implants.

The implant 10 can include a moldable body 12 that can be shaped by a surgeon during the implantation procedure or can be shaped prior to the implantation procedure. As diagrammatically illustrated in FIGS. 1 and 2, the implant 10 can define an upper pole 14 and a lower pole 16 separated by an axis 18. The implant 10 can also define a right side 20 and a left side 22 separated by an axis 24. The implant can further define an anterior side 26 and a posterior side 28 separated by an axis 30.

During sub-glandular breast reconstruction, the implant 10 can be implanted between the pectoral muscles and the breast tissue of the patient. Although the compositions discussed herein cover or substantially cover the entire surface area of the implant 10, the lower pole 16 and/or the right and left sides 20, 22 may require the most support post-implantation. As such, in certain embodiments, the portions of the composition covering the lower pole 16 and/or the right and left sides 20, 22 can define a continuous structure (e.g., without mesh patterns), while the remaining portions of the composition include mesh patterns formed therein. In certain embodiments, the portions of the composition covering the anterior side 26 can define a continuous structure, while the remaining portions of the composition include mesh patterns formed therein.

Similarly, adjunct fat injection techniques may be used on the upper pole 14 of the breast. Therefore, in certain embodiments, rather than a mesh pattern, a continuous structure can be maintained at the upper pole 14 region of the composition to provide protection from medical devices used during the adjunct fat injection technique, while remaining portions of the composition include mesh patterns formed therein. However, it should be understood that a variety of configurations including continuous structures and mesh patterns are contemplated to provide adequate support to regions of the implant 10 during and post-implantation.

Figure 3:
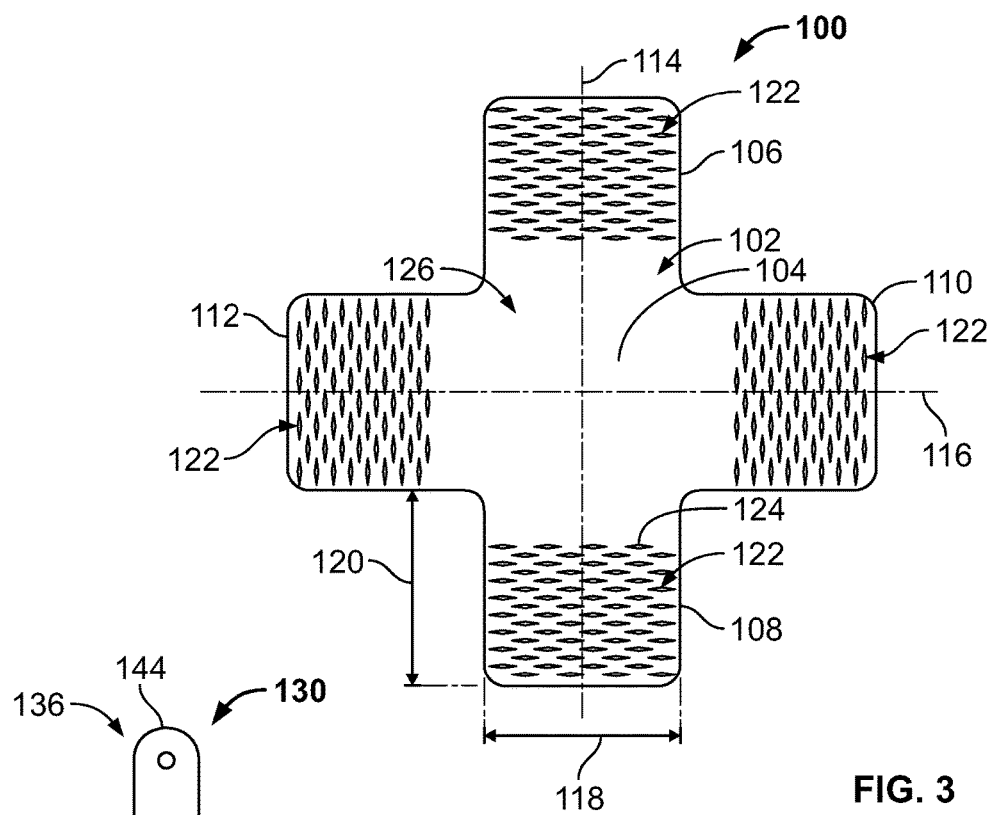
FIG. 3 is a front view of a composition, according to certain embodiments.

With reference to FIG. 3, a front view of one embodiment of an exemplary composition 100 is shown. In certain embodiments, the composition 100 can be made from processed tissue, e.g., an acellular tissue matrix, an acellular dermal matrix, or the like. In certain embodiments, the composition 100 can be made from a synthetic material. In certain embodiments, the composition 100 can be made from a combination of processed tissue and synthetic materials.

The composition 100 includes a composition body 102. The composition body 102 can be shaped or formed into a substantially flat or sheet-like configuration. However, the composition body 102 can be flexible such that the composition body 102 can conform to and wrap around the three-dimensional shape of the implant 10. The composition body 102 includes a central region 104 from which extensions 106-112 protrude or extend.

The central region 104 can define a substantially rectangular configuration. The first extension 106 (e.g., a top extension) and the second extension 108 (e.g., a bottom extension) can extend from the central region 104 in a substantially parallel manner relative to each other and a vertical axis 114. The third extension 110 (e.g., a right extension) and the fourth extension 112 (e.g., a left extension) can extend from the central region 104 in a substantially parallel manner relative to each other and a horizontal axis 116. The vertical axis 114 can be substantially perpendicular to the horizontal axis 116. As such, the first and second extensions 106, 108 can extend substantially perpendicularly relative to the third and fourth extensions 110, 112.

Each of the extensions 106-112 can define a substantially similar width 118, length 120, or both. In certain embodiments, one or more of the extensions 106-112 can define a different width 118, length 120, or both, as compared to the other extensions 106-112. Although illustrated as defining a substantially rectangular configuration, one or more of the extensions 106-112 can define, e.g., a square shape, a rectangular shape, an oval shape, or the like. In certain embodiments, the edges of the extensions 106-112 can be curved. In certain embodiments, the edges of the extensions 106-112 can be angled or pointed.

In certain embodiments, the composition 100 can include one or more mesh patterns 122 formed therein. For example, the composition 100 can include a mesh pattern 122 formed on a portion or the entire surface area of, e.g., the central region 104, the first extension 106, the second extension 108, the third extension 110, the fourth extension 112, combinations thereof, or the like. In certain embodiments, the mesh pattern 122 can extend from one area of the composition body 102 into another area of the composition 102. For example, as shown in FIG. 3, the mesh pattern 122 can extend from the second extension 108 into a portion of the central region 104.

The mesh pattern 122 can include a plurality of slits 124 (e.g., perforations, openings, or the like) formed in and passing through the composition body 102. Portions of the composition body 102 including the mesh pattern 122 can be stretched and expanded due to the pattern of slits 124 such that the length of the portion of the composition body 102 can be increased or adjusted based on the size of the implant 10.

In certain embodiments, each slit 124 can be dimensioned equally. In certain embodiments, the slits 124 can have different dimensions. In certain embodiments, the slits 124 can be dimensioned between approximately 10 mm to approximately 15 mm in length. In certain embodiments, the slits 124 can be dimensioned between approximately 12 mm and approximately 15 mm in length. The slits 124 of the mesh patterns 122 formed on the first and second extensions 106, 108 can be substantially parallel to each other and the horizontal axis 116. The slits 124 of the mesh patterns 122 formed on the third and fourth extensions 110, 112 can be substantially parallel to each other and the vertical axis 114. In certain embodiments, the slits 124 can be linear in form. In certain embodiments, the slits 124 can be curved in form. In certain embodiments, each row of slits 124 can be staggered or offset relative to the adjacent row of slits 124. In certain embodiments, each row of slits 124 can be staggered or offset relative to the adjacent row of slits 124 by approximately 8 mm to approximately 10 mm. In certain embodiments, each row of slits 124 can be spaced from the adjacent row of slits 124 by approximately five mm or less. However, it should be understood that alternative distance ranges can be used to optimize the size and/or stretching of the composition 100.

Although illustrated as a plurality of slits, in certain embodiments, the mesh patterns discussed herein can be formed from any pattern of holes or openings. For example, in certain embodiments, the mesh patterns can be formed from a pattern of circular holes spaced relative to each other such that the composition can be stretched and expanded at the mesh patterns. As a further example, in certain embodiments, the mesh patterns can be formed from a pattern of oval holes spaced relative to each other such that the composition can be stretched and expanded at the mesh patterns.

In certain embodiments, portions of the composition body 102 can define a continuous structure 126 (e.g., a structure without a mesh pattern 122 formed therein). Areas with a continuous structure 126 can be aligned with portions of the implant 10 that require the most amount of support or protection. The areas of the composition body 102 including the mesh pattern 122 and the continuous structure 126 can be customized depending on the type of implant 10 being used with the composition 100 and characteristics of the patient receiving the implant 10. For example, if a patient is known to have insufficient host tissue for supporting the implant on certain sides, the composition 100 can be customized to define a continuous structure 126 on those sides to provide added support to the implant 10. As a further example, the continuous structure 126 can be located on the area of the composition 100 that will be used to provide greater support to the lower pole 16 of the implant 10, while the mesh patterns 122 are formed to allow the extensions 106-112 to wrap around the remaining areas of the implant 10.

Figures 4, 5:
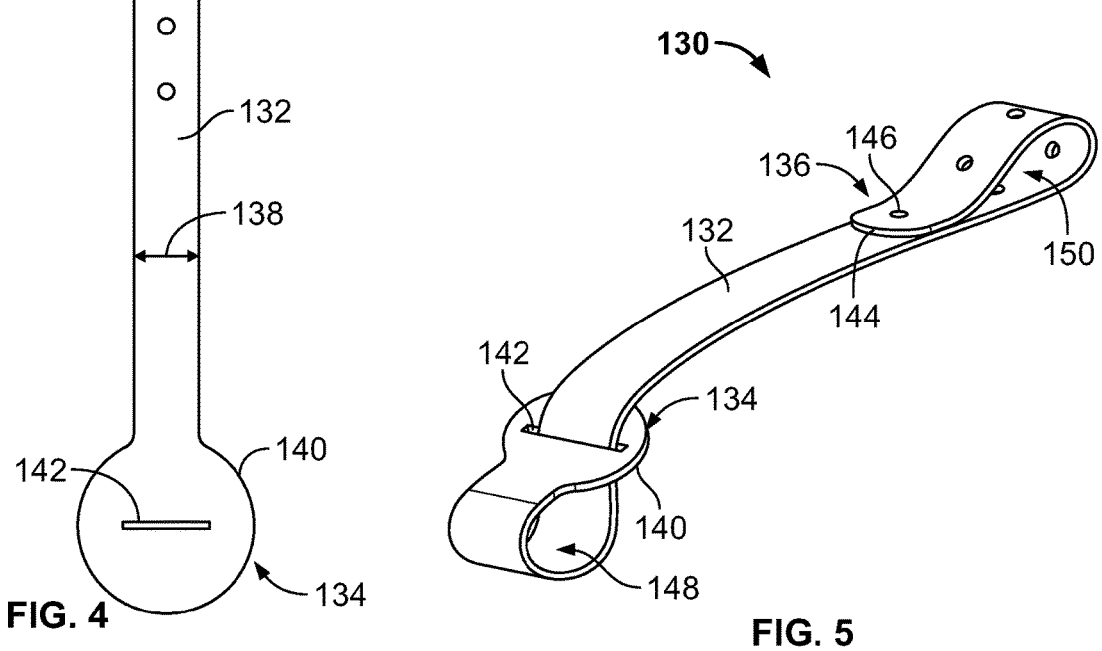
FIG. 4 is a front view of a fastening element, according to certain embodiments.
FIG. 5 is a perspective view of a fastening element, according to certain embodiments.

With reference to FIGS. 4 and 5, front and perspective views of one exemplary embodiment of a fastening element 130 are provided. The fastening element 130 can be formed from a tissue (e.g., an acellular tissue matrix, an acellular dermal matrix, or the like) and/or a synthetic material. As will be discussed in greater detail below, the fastening element 130 can be used to secure the composition 100 to the implant 10 in the wrapped configuration. The fastening element 130 can be in the form of an elongated strap including an elongated body 132 with a proximal end 134 and a distal end 136. The width 138 of the elongated body 132 can be dimensioned to pass freely through the slits 124 of the mesh patterns 122 formed in the composition 100. The fastening element 130 can be flexible to allow manipulation of the fastening element 130 when interlocking the fastening element 130 relative to components of the composition 100.

The proximal end 134 of the fastening element 130 can include a rounded tip 140. The diameter of the tip 140 can be dimensioned greater than the width 138 of the elongated body 138 to accommodate a slit 142 formed in the proximal end 134. The slit 142 can extend in a perpendicular direction relative to the elongated body 138 extending from the tip 140. The slit 142 can pass through the tip 140 and provides an aperture through which the distal end 136 and the elongated body 132 can pass. In particular, the slit 142 can be dimensioned to allow passage of the distal end 136 and the elongated body 132 therethrough. In certain embodiments, the slit 142 can be dimensioned slightly greater than the width 138 of the elongated body 132.

The distal end 136 of the fastening element 130 can define a rounded tip 144. The rounded tip 144 can provide an easier configuration for passing into the slit 142 of the proximal end 134. Starting from a position spaced from the tip 144, the elongated body 132 can include one or more suture holes or apertures 146 formed in and passing through the elongated body 132. In certain embodiments, the apertures 146 can be formed from the distal end 136 up to the slit 142 of the proximal end 134. In certain embodiments, the apertures 146 can be formed from the distal end 136 a partial distance in the direction of the slit 142 of the proximal end 134. The apertures 146 can be configured and dimensioned to allow suture to be passed therethrough for securing the distal end 136 to the elongated body 102.

As shown in FIG. 5, during assembly, the distal end 136 of the fastening element 130 can initially be snaked or passed through a slit 124 in the mesh pattern 122 in the composition 100, and further passed through the slit 142 in the proximal end 134 of the fastening element 130. A first loop 148 can thereby be formed to secure the fastening element 130 to a first portion of the composition 100.

The distal end 136 is further snaked or passed through a slit 124 in another mesh pattern 122 of the composition 100, and folded over to align two of the apertures 146. A second loop 150 can thereby be formed to secure the fastening element 130 to a second portion of the composition 100. The apertures 146 used for alignment to create the second loop 150 can be selected based on the desired tension between the first and second portions of the composition 100, e.g., the desired tension to maintain the composition 100 wrapped around the implant 10. In certain embodiments, if insufficient tension is created by the fastening element 130, the fastening element 130 can be passed through alternative openings 152 in the mesh pattern 122 away from the edge of the extension 106-112 such that certain extensions 106-112 overlap relative to each other to create the desired tension. Suture can be passed through the aligned apertures 146 to secure the distal end 136 to the elongated body 132, and to maintain the fastening element 130 interlocked relative to the composition 100.

Figure 6:
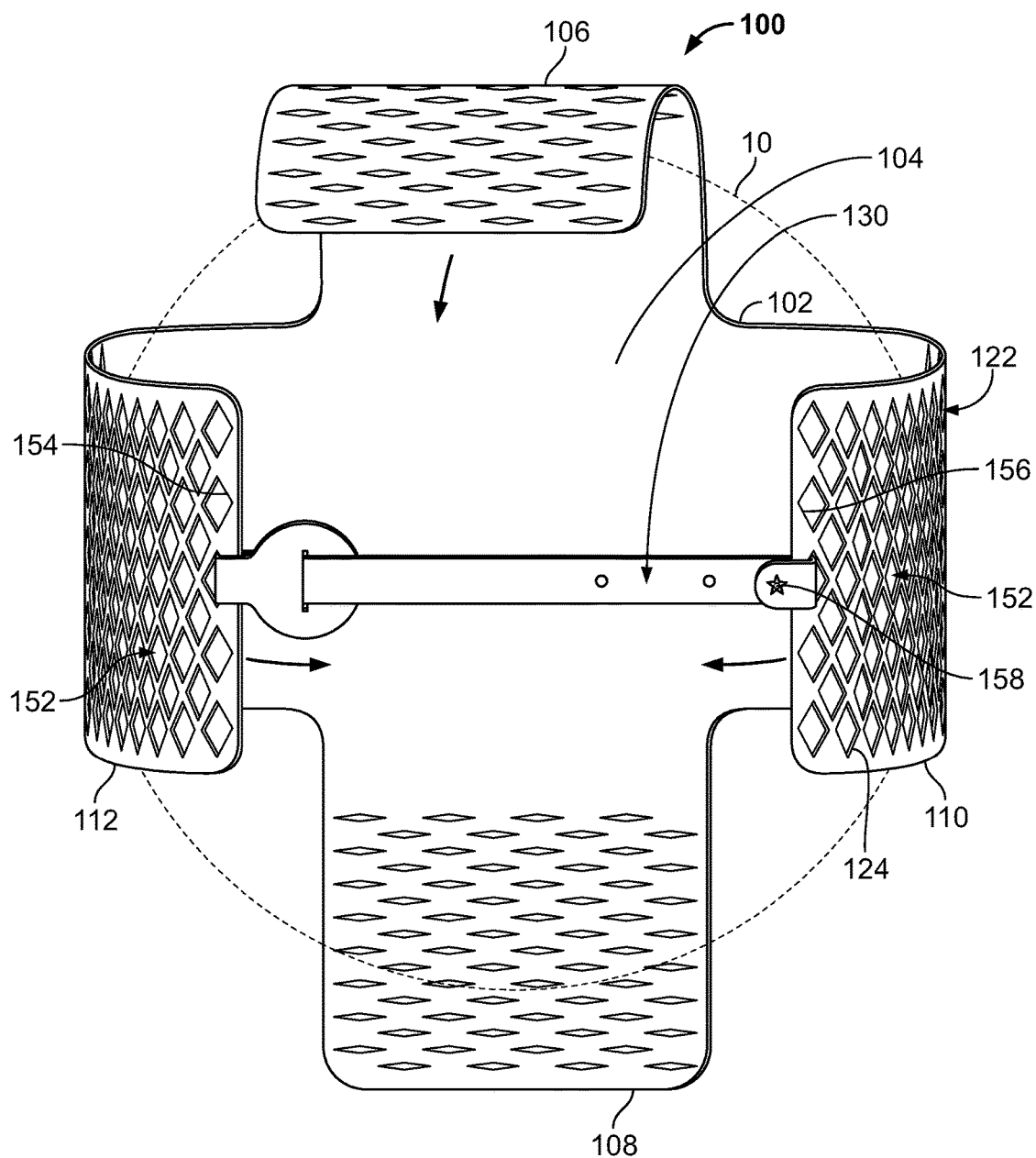
FIG. 6 is a perspective view of a composition in a partially wrapped configuration relative to a breast implant or tissue expander, according to certain embodiments.

With respect to FIG. 6, a perspective view of the composition 100 being wrapped around the implant 10 is shown. Initially, the implant 10 can be positioned on and orientated relative to the composition 100 such that the appropriate sections of the implant 10 that require additional support are positioned adjacent to continuous structure 126 portions of the composition 100. For example, the lower pole 16 and the anterior side 26 of the implant 10 can be positioned against continuous structure 126 portions of the composition 100. With respect to the lower pole 16, a greater amount of support may be desired due to most of the weight of the implant 10 being relayed to the bottom breast tissue post-implantation.

In the initial configuration, the composition 100 can be dimensioned smaller than the surface area of the implant 10. However, as shown in FIG. 6, one or more extensions 106-112 can include mesh patterns 122 for expanding and stretching portions of the composition 100 to wrap the composition 100 around the implant 10 (e.g., to completely or nearly completely surround the implant 10). As discussed herein, completely or nearly completely surrounding, covering or wrapping the implant 10 indicates that the composition 100 stretches or expands over a major portion of the surface area of the implant 10. Thus, although the composition 100 includes mesh patterns 122 that stretch and expand to create openings exposing portions of the implant 10 therethrough, it should be understood that the composition 100 is still considered as surrounding, covering or wrapping the implant 10.

For example, the third and fourth extensions 110, 112 are shown stretched in FIG. 6 to wrap around the right side 20, left side 22 and posterior side 28 of the implant 10. The mesh patterns 122 can be expanded and stretched by applying a tensile force on the respective extension 106-112 associated with the mesh pattern 122. The slits 124 that form the mesh pattern 122 can expand due to the tensile force to create a plurality of openings 152 that are dimensioned greater than the slits 124 in the non-expanded configuration. The expanded and stretched mesh patterns 122 allow the composition 100 to conform to the size and/or shape of the implant 10. As such, less material is necessary to wrap the composition 100 nearly completely or completely around the implant 10.

In order to secure portions of the composition 100 around the implant 10 in a wrapped configuration, one or more fastening elements 130 can be used. As discussed above, the distal end 136 of the fastening element 130 can be passed through an opening 152 (e.g., the opening 152 in the fourth extension 112) and further passed through the slit 142 formed in the proximal end 134 of the fastening element 130. The first loop 148 formed at the proximal end 134 of the fastening element 130 can thereby be passed around and interlocked with a strip 154 of material surrounding the opening 152 and, thereby, the fourth extension 112.

The distal end 136 can further be passed through the opening 152 in a different mesh pattern 122 (e.g., the opening 152 in the third extension 110). In certain embodiments, the second loop 150 can be formed around a mesh pattern 122 in an extension 106-112 opposing the extension 106-112 around which the first loop 148 is formed. After passing the distal end 136 through the opening 152, the fastening element 130 can be used to tighten the first and second extensions 110, 112 relative to each other until the desired amount of wrapping of the composition 100 around the implant is achieved. In certain embodiments, the third and fourth extensions 110, 112 can be stretched until the third and fourth extensions 110, 112 are in a touching relation, thereby wrapping around the entire posterior side 28 of the implant 10. In certain embodiments, the third and fourth extensions 110, 112 can be stretched and remain in a spaced relation relative to each other, thereby leaving a portion of the posterior side 28 of the implant 10 exposed. However, in such embodiments, support to the implant 10 can naturally be provided by the chest wall and/or the pectoral muscle against which the implant 10 is positioned. Thus, the composition 100 completely or nearly completely surrounds the surface area of the implant 10.

The distal end 136 can be folded over the strip 156 of material surrounding the opening 152 and two apertures 146 in the fastening element 130 can be aligned. Suture 158 can be passed through the apertures 146 to secure the second loop 150 around the strip 156, thereby interlocking the fastening element 130 to the third extension 110. In certain embodiments, suture 158 can be passed through the elongated body 132 without the use of the apertures 146. The fastening element 130 therefore stretches between the third and fourth extensions 110, 112 and around a portion of the implant 10. The fastening element 130 can thereby maintain the third and fourth extensions 110, 112 wrapped around the implant 10. In certain embodiments, suture can be used to secure the extensions 106-112 relative to each other.

Figure 7:
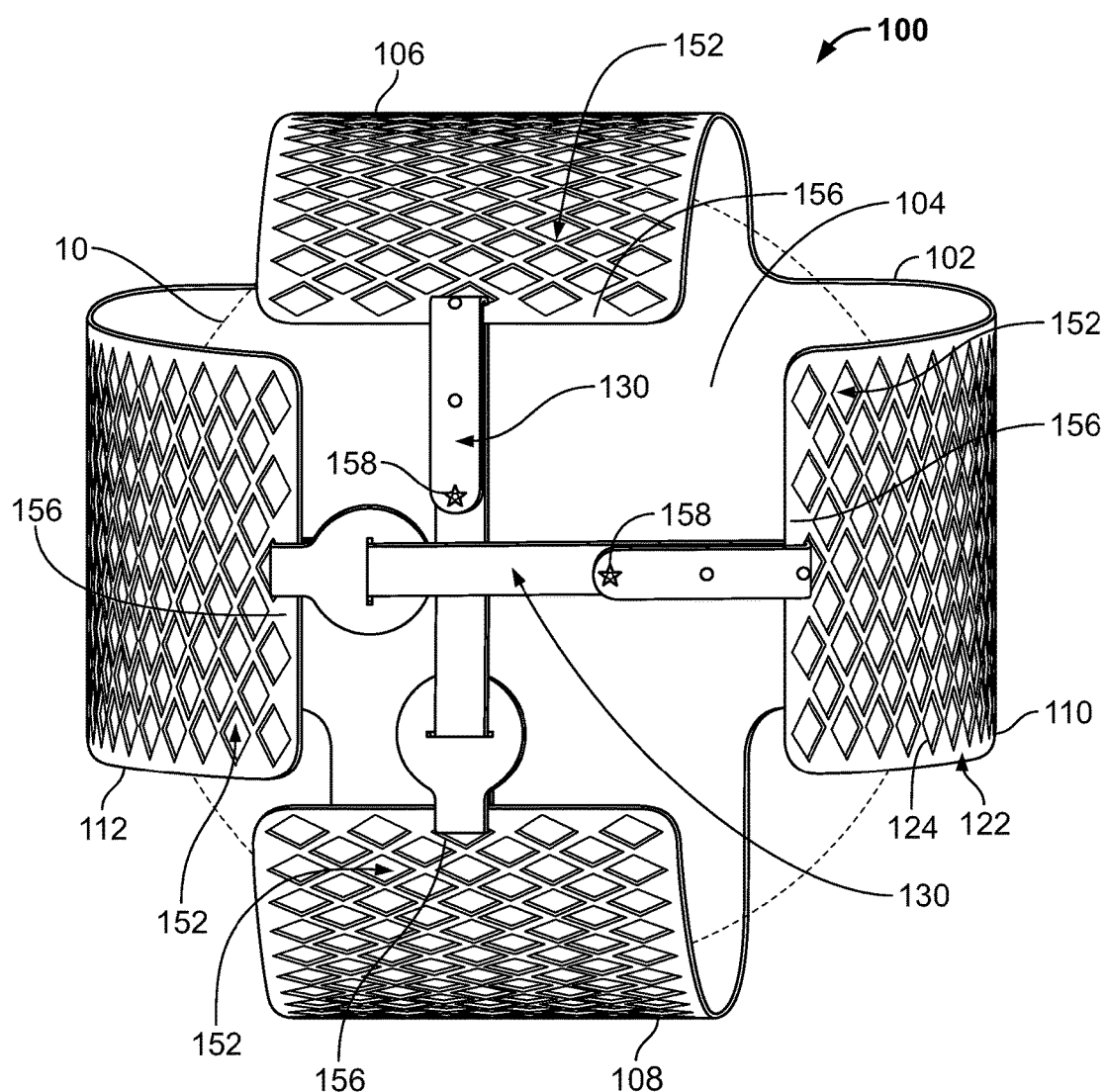
FIG. 7 is a perspective view of a composition in a partially wrapped configuration relative to a breast implant or tissue expander, according to certain embodiments.

With respect to FIG. 7, a perspective view of the composition 100 being wrapped around the implant 10 is shown. The composition 100 can be wrapped completely or nearly completely around the implant 10 in a substantially similar manner to that described with respect to FIG. 6. However, rather than using a single fastening element 130, two or more fastening elements 130 can be used to secure the opposing extensions 106-112 relative to each other. For example, a first fastening element 130 can be used to secure the first and second extensions 106, 108 relative to each other, and a second fastening element 130 can be used to secure the third and fourth extensions 110, 112 relative to each other. It should be understood that any number of fastening elements 130 can be used to secure the composition 100 in a wrapped configuration around the implant 10.

In certain embodiments, one fastening element 130 can be used to secure three or more extensions 106-112 relative to each other. For example, after the fastening element 130 has been interlocked relative to one extension, e.g., the first extension 106, the distal end can be passed through the openings of the third, second and fourth extensions 110, 106, 112 and interlocked relative to the fourth extension 112. A single fastening element 130 can thereby be used to maintain each extension 106-112 wrapped around the implant 10.

Figure 8:
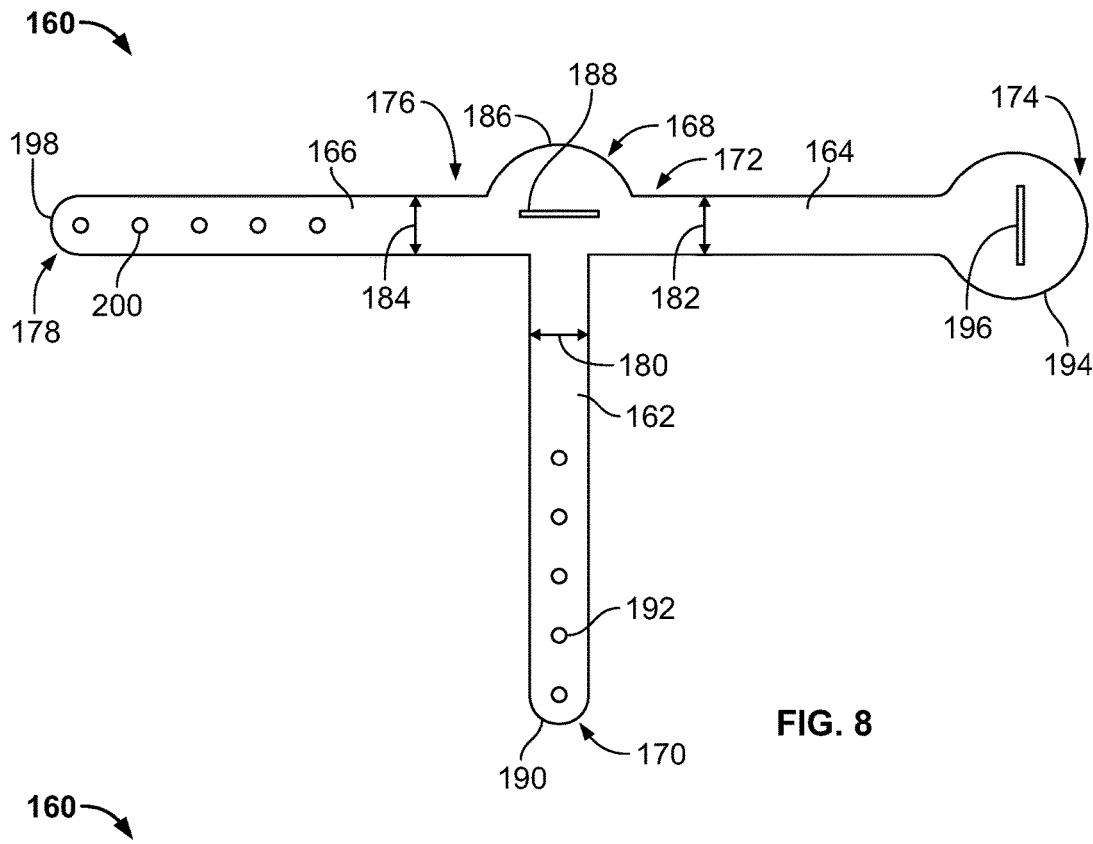
FIG. 8 is a front view of a fastening element, according to certain embodiments.
Figure 9:
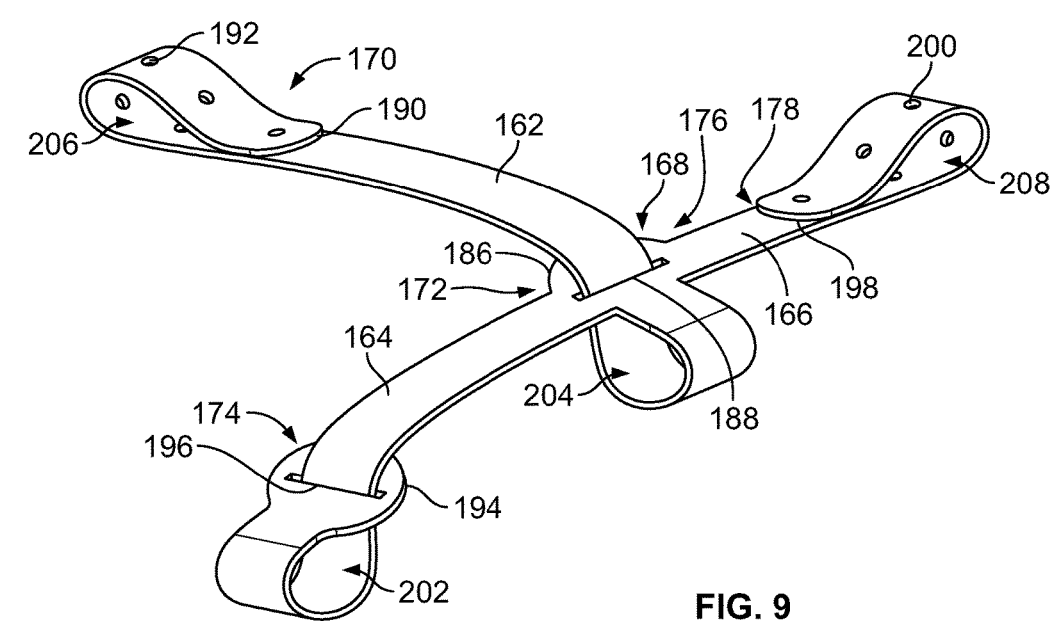
FIG. 9 is a perspective view of a fastening element, according to certain embodiments.

With reference to FIGS. 8 and 9, front and perspective views of another exemplary embodiment of a fastening element 160 are provided. The fastening element 160 can be formed from a tissue (e.g., an acellular tissue matrix, an acellular dermal matrix, or the like) and/or a synthetic material. As will be discussed in greater detail below, the fastening element 160 can be used to secure the composition 100 to the implant 10 in the wrapped configuration.

The fastening element 160 can be in the form of a substantially T-shaped strap including a vertical elongated body 162, a first horizontal elongated body 164, and a second horizontal elongated body 166. The vertical elongated body 162 can define a proximal end 168 and a distal end 170. The first and second horizontal elongated bodies 164, 166 can extend in a substantially parallel manner relative to each other from opposing sides of the proximal end 168 of the vertical elongated body 162. In particular, the first and second horizontal elongated bodies 164, 166 can extend in a substantially perpendicular manner relative to the vertical elongated body 162.

The first horizontal elongated body 164 can define a proximal end 172 and a distal end 174. The proximal end 172 of the first horizontal elongated body 164 can be formed integrally with the proximal end 168 of the vertical elongated body 162. The first horizontal elongated body 164 thereby connects to the vertical elongated body 162 at the proximal end 172. The second horizontal elongated body 166 can define a proximal end 176 and a distal end 178. The proximal end 178 of the second horizontal elongated body 166 can be formed integrally with the proximal end 168 of the vertical elongated body 162. The second horizontal elongated body 166 thereby connects to the vertical elongated body 162 at the proximal end 176.

The vertical elongated body 162 and the first and second horizontal elongated bodies 164, 166 can define widths 180-184, respectively, can be dimensioned to pass freely through the slits 124 of the mesh patterns 122 formed in the composition 100. The fastening element 160 can be flexible to allow manipulation of the fastening element 160 when interlocking the fastening element 160 relative to components of the composition 100.

In certain embodiments, the proximal end 168 of the vertical elongated body 162 can include a rounded tip 186. The diameter of the rounded tip 186 can be dimensioned greater than the width 180 of the vertical elongated body 162 to provide a stronger structure for attachment of the first and second horizontal elongated bodies 164, 166. The rounded tip 186 can accommodate a slit 188 formed in the proximal end 168. The slit 188 can extend in a perpendicular direction relative to the vertical elongated body 162 extending from the tip 186 and substantially parallel to the first and second horizontal elongated bodies 164, 166. The slit 188 can pass through the tip 186 and provides an aperture through which the distal end 170 and the vertical elongated body 162 can pass. In particular, the slit 188 can be dimensioned to allow passage of the distal end 170 and the vertical elongated body 162 therethrough. In certain embodiments, the slit 188 can be dimensioned slightly greater than the width 180 of the vertical elongated body 162.

The distal end 170 of the vertical elongated body 162 can define a rounded tip 190. The rounded tip 190 can provide an easier configuration for passing into the slit 188 of the proximal end 168. Starting from a position spaced from the tip 190, the vertical elongated body 162 can include one or more suture holes or apertures 192 formed in and passing through the vertical elongated body 162. In certain embodiments, the apertures 192 can be formed from the distal end 170 up to the slit 188 of the proximal end 168. In certain embodiments, the apertures 192 can be formed from the distal end 170 a partial distance in the direction of the slit 188 of the proximal end 168. The apertures 192 can be configured and dimensioned to allow suture therethrough for securing the distal end 170 to the vertical elongated body 162.

In certain embodiments, the distal end 174 of the first horizontal elongated body 164 can include a rounded tip 194. The diameter of the rounded tip 194 can be dimensioned greater than the width 182 of the first horizontal elongated body 164. The rounded tip 194 can accommodate a slit 196 formed in the distal end 174. The slit 196 can extend in a perpendicular direction relative to the first horizontal elongated body 164 extending from the tip 194 and substantially parallel to the vertical elongated body 162. The slit 196 can pass through the tip 194 and is dimensioned to provide an aperture through which the vertical elongated body 162, the second horizontal elongated body 166, and the first horizontal elongated body 164 can pass. As will be discussed in greater detail below, the flexibility of the fastening element 160 allows portions of the fastening element 160 to be folded and passed through the slit 196.

The proximal end 172 of the first horizontal elongated body 164 can be connected to the proximal end 168 of the vertical elongated body 162. Other than the slit 196, the first horizontal elongated body 164 can define a continuous and aperture-free material.

The proximal end 176 of the second horizontal elongated body 166 can be connected to the proximal end 168 of the vertical elongated body 162. The distal end 178 of the second horizontal elongated body 166 can define a rounded tip 198. The rounded tip 198 can provide an easier configuration for passing into the slit 198 of the distal end 174 of the first horizontal elongated body 164. Starting from a position spaced from the tip 198, the second horizontal elongated body 166 can include one or more suture holes or apertures 200 formed in and passing through the second horizontal elongated body 166. In certain embodiments, the apertures 200 can be formed from the distal end 178 up to the slit 188 of the proximal end 168 of the vertical elongated body 162. In certain embodiments, the apertures 200 can be formed from the distal end 178 a partial distance in the direction of the slit 188 of the proximal end 168 of the vertical elongated body 162. The apertures 200 can be configured and dimensioned to allow suture therethrough for securing the distal end 178 to the second horizontal elongated body 166.

As shown in FIG. 9, during assembly, distal end 174 of the first horizontal elongated body 164 can initially be snaked or passed through a slit 124 in the mesh pattern 122 in the composition 100. The vertical elongated body 162 and the second horizontal elongated body 166 can then be snaked or passed through the slit 196 of the distal end 174. For example, the vertical elongated body 162 can be folded onto the second horizontal elongated body 166 (e.g., to substantially align the distal ends 170, 178) and the distal ends 170, 178 can be snaked or passed through the slit 196. A first loop 202 can thereby be formed to secure the fastening element 160 to a first portion of the composition 100 (e.g., a fourth extension 112).

Next, the distal end 170 of the vertical elongated body 162 can be snaked or passed through a slit 124 in another mesh pattern 122 in the composition (e.g., the second extension 108). The distal end 170 of the vertical elongated body 162 can further be snaked or passed through the slit 188 of the vertical elongated body 162. A second loop 204 can thereby be formed to secure the fastening element 160 to a second portion of the composition 100 (e.g., the second extension 108).

Next, the distal end 170 of the vertical elongated body 162 can be snaked or passed through a slit 124 in another mesh pattern 122 of the composition 100 (e.g., the first extension 106), and folded over to align two of the apertures 192. A third loop 206 can thereby be formed to secure the fastening element 160 to a third portion of the composition 100 (e.g., the first extension 106). The apertures 192 used for alignment to create the third loop 206 can be selected based on the desired tension between the second and third portions of the composition 100, e.g., the desired tension to maintain the second and third portions of the composition 100 wrapped around the implant 10. Suture can be passed through the aligned apertures 192 to secure the distal end 170 to the vertical elongated body 162, and to maintain the fastening element 160 interlocked relative to the third portion of the composition 100.

As a final step, the distal end 178 of the second horizontal elongated body 166 can be snaked or passed through a slit 124 in another mesh pattern 122 of the composition 100 (e.g., the third extension 110), and folded over to align two of the apertures 200. A fourth loop 208 can thereby be formed to secure the fastening element 160 to a fourth portion of the composition 100 (e.g., the third extension 110). The apertures 200 used for alignment to create the fourth loop 208 can be selected based on the desired tension between the first and fourth portions of the composition 100, e.g., the desired tension to maintain the first and fourth portions of the composition 100 warped around the implant 10. In certain embodiments, if insufficient tension is created by the fastening element 160, the fastening element 160 can be passed through alternative openings 152 in the mesh pattern 122 away from the edge of the extension 106-112 such that certain extensions 106-112 overlap relative to each other to create the desired tension. Suture can be passed through the aligned apertures 200 to secure the distal end 178 to the second horizontal elongated body 166, and to maintain the fastening element 160 interlocked relative to the fourth portion of the composition 100.

Figure 10:
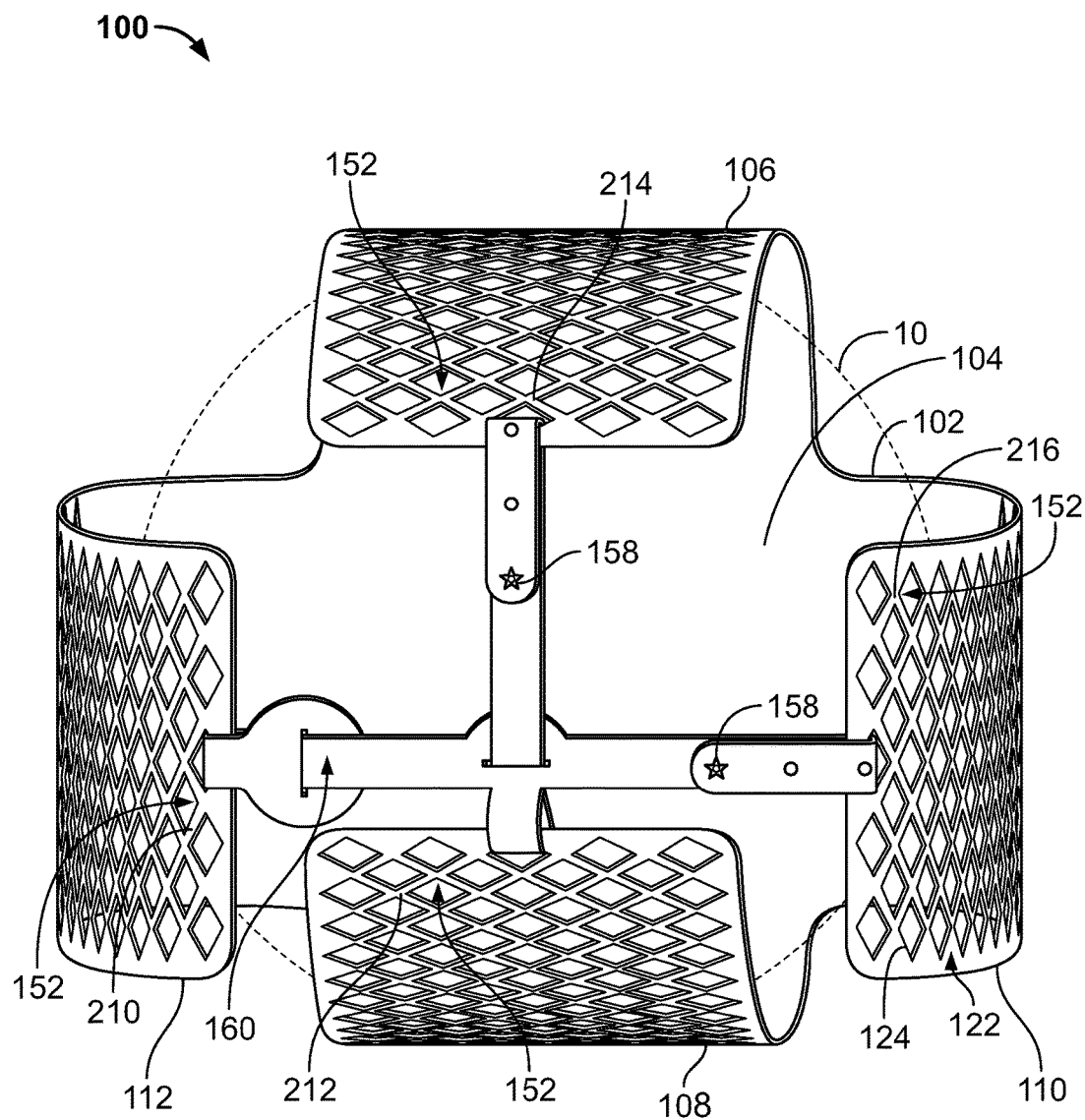
FIG. 10 is a perspective view of a composition in a partially wrapped configuration relative to a breast implant or tissue expander, according to certain embodiments.

With respect to FIG. 10, a perspective view of the composition 100 being wrapped around the implant 10 is shown. Positioning and orientation of the implant 10 relative to the composition 100 can be substantially similar to the process described with respect to FIG. 6. However, rather than using one or two fastening elements 130 to secure portions of the composition 100 around the implant 10 in a wrapped configuration, a single fastening element 160 can be used to secure all four extensions 106-112 relative to each other.

As described above, the fastening element 160 can be used to create loops 202-208 to interlock the fastening element 160 relative to respective extensions 106-112 of the composition 100. For example, the first loop 202 can be formed relative to the opening 152 and the strip 210 of material surrounding the opening 152 in the fourth extension 112. The second loop 204 can be formed relative to the opening 152 and the strip 212 of material surrounding the opening 152 in the second extension 108. The third loop 206 can be formed relative to the opening 152 and the strip 214 of material surrounding the opening 152 in the first extension 106. The fourth loop 208 can be formed relative to the opening 152 and the strip 216 of material surrounding the opening 152 in the third extension 110. However, it should be understood that the fastening element 160 can be orientated differently relative to the composition 100 such that loops 202-208 are used to secure the fastening element 160 to alternative extensions 106-112. Suture 158 can be passed through the apertures 192, 200 to secure the loops 206, 208 around the strips 214, 216, respectively, thereby interlocking the fastening element 160 to two of the extensions 106-112. In certain embodiments, suture 158 can be passed through the elongated body 162, 166 without the use of the apertures 192, 200.

The vertical elongated body 162 can therefore be used to secure two portions of the composition 100 (e.g., the first and second extensions 106, 108) relative to each other and in the wrapped configuration around the implant 10. In particular, the passage of the distal end 170 of the vertical elongated body 162 through the opening 152 in the first extension 106 can be varied to increase or decrease the tension and distance between the first and second extensions 106, 108, thereby allowing adjustment of the amount of surface area of the implant 10 wrapped by the composition 100.

The first and second horizontal elongated bodies 164, 166 can be used to secure two alternative portions of the composition 100 (e.g., the third and fourth extensions 110, 112) relative to each other and in the wrapped configuration around the implant 10. In particular, the passage of the distal end 178 of the second horizontal elongated body 166 through the opening 152 in the fourth extension 112 can be varied to increase or decrease the tension and distance between the third and fourth extensions 110, 112, thereby allowing adjustment of the amount of surface area of the implant 10 wrapped by the composition 100.

In certain embodiments, the extensions 106-112 can be stretched until the two or more of the extensions 106-112 are in a touching relation, thereby wrapping around the entire posterior side 28 of the implant 10. In certain embodiments, the two or more of the extensions 106-112 can be stretched and remain in a spaced relation relative to each other, thereby leaving a portion of the posterior side 28 of the implant 10 exposed. However, in such embodiments, support to the implant 10 can naturally be provided by the chest wall and/or the pectoral muscle against which the implant 10 is positioned. Thus, the composition 100 completely or nearly completely surrounds the surface area of the implant 10.

Figure 11:
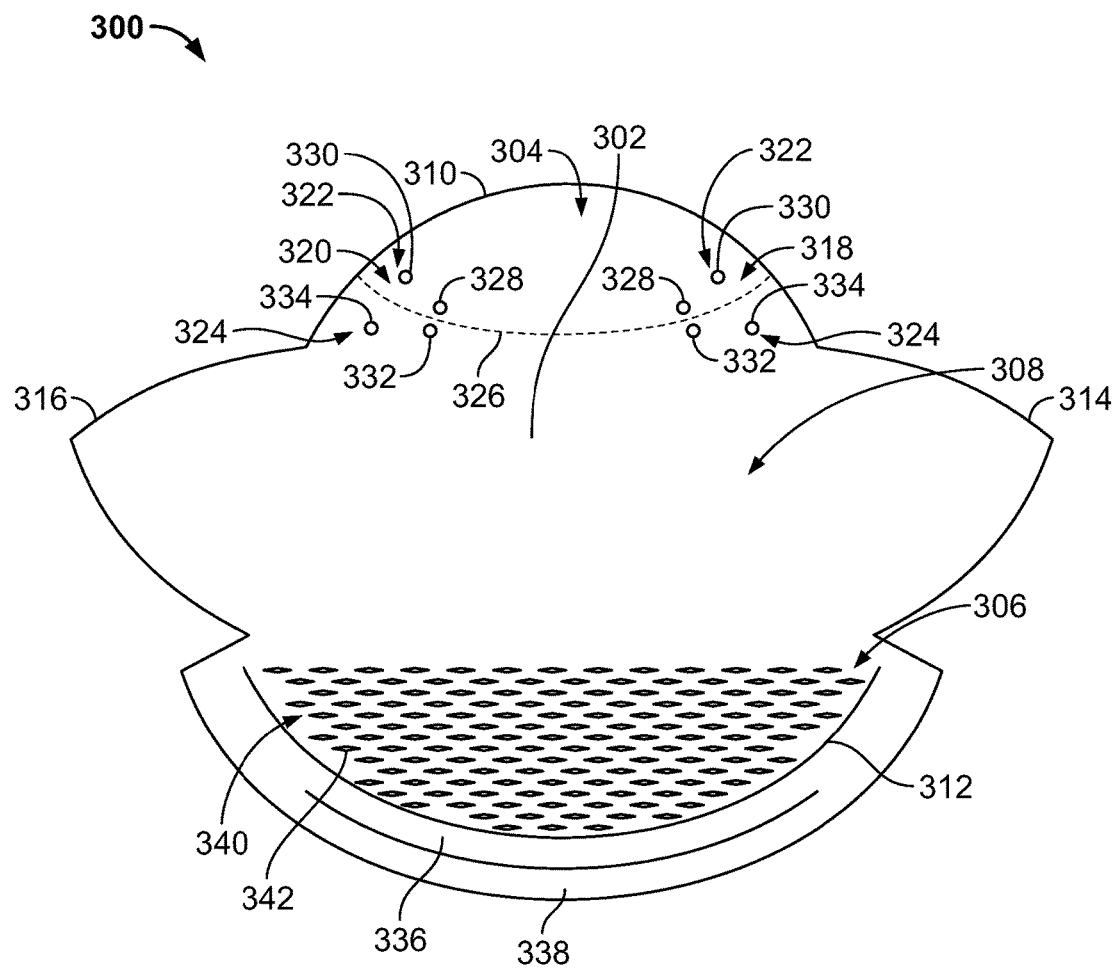
FIG. 11 is a front view of a composition, according to certain embodiments.

With reference to FIG. 11, a front view of another embodiment of an exemplary composition 300 is shown. In certain embodiments, the composition 300 can be made from processed tissue, e.g., an acellular tissue matrix, an acellular dermal matrix, or the like. In certain embodiments, the composition 300 can be made from a synthetic material. In certain embodiments, the composition 300 can be made from a combination of processed tissue and synthetic materials.

The composition 300 includes a composition body 302. The composition body 302 can be shaped or formed into a substantially flat or sheet-like configuration. However, the composition body 302 can be flexible such that the composition body 302 can conform to and wrap around the three-dimensional shape of the implant 10.

The composition body 302 includes a top region 304, a bottom region 306, and a central region 308 disposed between the top and bottom regions 304, 306. The top region 304 can define a substantially semi-circular form 310 extending from the central region 308. The bottom region 306 can define a substantially semi-circular form 312 extending from an opposing side of the central region 308 relative to the top region 304. The central region 308 includes a first flap 314 and a second flat 316 extending therefrom on opposing sides of the central region 308. In certain embodiments, the first and second flaps 314, 316 can define pointed ends with curved sides. In certain embodiments, the first and second flaps 314, 316 can define pointed ends with linear sides.

In certain embodiments, the top region 304 can include two groups 318, 320 of apertures formed therein. The groups 318, 320 of apertures can be formed on opposing sides of the top region 304 in a spaced manner. Each group 318, 320 can include a first pair of apertures 322 and a second pair of apertures 324. The first and second pair of apertures 322, 324 can be positioned on opposing sides of a fold line 326. In certain embodiments, the fold line 326 can be formed in the composition body 302 to assist in folding the top region 304 over the implant 10. In certain embodiments, the composition body 302 does not include a fold line 326 and the fold line 326 shown in FIG. 11 is provided for illustrative purposes only.

The first pair of apertures 322 includes a first aperture 328 and a second aperture 330. The second pair of apertures 324 includes a first aperture 332 and a second aperture 334. The first and second pair of apertures 322, 324 can be disposed on opposing sides of the fold line 326 such that when the top region 304 is folded along the fold line 326, the first apertures 328, 332 and the second apertures 330, 334 align for suture passage therethrough. Thus, in embodiments including a fold line 326 formed in the composition body 302, the fold line 326 can assist with aligning the first and second pair of apertures 322, 324 relative to each other.

In certain embodiments, the bottom region 306 can include one or more straps formed therein, e.g., a first strap 336 and a second strap 338. In particular, the first and second straps 336, 338 can be formed directly in the composition body 302. For example, the first strap 336 can be formed from material directly adjacent to the semi-circular form 312 and the second strap 338 can be formed from material directly adjacent to the first strap 336. The straps 336, 338 can therefore extend from one edge to the opposite edge of the bottom region 306 spanning the width of the bottom region 306. In certain embodiments, the composition 300 can include one or more straps formed adjacent to the top region 304.

Each strap 336, 338 can define an elongated body that can be configured and dimensioned to be extended over portions of the implant 10 to maintain the composition 300 in a wrapped configuration relative to the implant 10. In particular, the straps 336, 338 can be stretched and fit over portions of the implant 10, and the flexible material of the composition 300 allows the straps 336, 338 to stay in place and maintain a pressure on the implant 10 sufficient to prevent undesired unwrapping of the composition 300. For example, the first strap 336 can be used to extend onto the upper pole 14 of the implant 10. As a further example, the second strap 338 can be used to extend onto the lower pole 16 of the implant 10.

Although illustrated with two straps 336, 338, in certain embodiments, the composition 300 can include a single strap (e.g., strap 336) that can sufficiently maintain the composition 300 wrapped around the implant 10. In certain embodiments, the composition 300 can include two or more straps that provide an even distribution of tension on the implant 10 to maintain the composition 300 in a wrapped configuration . . . .

In certain embodiments, one or more portions or areas of the composition 300 can include a mesh pattern 340 formed therein. As shown in FIG. 11, in certain embodiments, the bottom region 306 can include a mesh pattern 340 formed on all or a portion of the surface area thereof. In certain embodiments, the mesh pattern 340 can be formed on all or a portion of the surface area of, e.g., the top region 304, the central region 308, the bottom region 306, the first flap 314, the second flap 316, combinations thereof, or the like. In certain embodiments, the mesh pattern 340 can extend from one area into another area of the composition body 302. The location or formation of the mesh pattern 340 can be selected based on the areas of the implant 10 that require the most and least support. For example, areas of the implant 10 requiring less support can be covered by portions of the composition 300 including the mesh pattern 340, while areas of the implant 10 requiring more support can be covered by portions of the composition 300 including the continuous structure (e.g., without a mesh pattern 340, such as the central region 308 of FIG. 11).

The mesh pattern 340 can be substantially similar to the mesh pattern 122 discussed above. In particular, the mesh pattern 340 can include a plurality of slits 342. In certain embodiments, the slits 342 can be formed in a horizontal direction. In certain embodiments, the slits 342 can be formed in a vertical direction. In certain embodiments, each row of adjacent slits 342 can be staggered relative to each other. Imparting a tensile force on any portions of the composition 300 including the mesh pattern 340 allows the composition body 302 to stretch and expand to cover the three-dimensional form of the implant 10.

Figure 12:
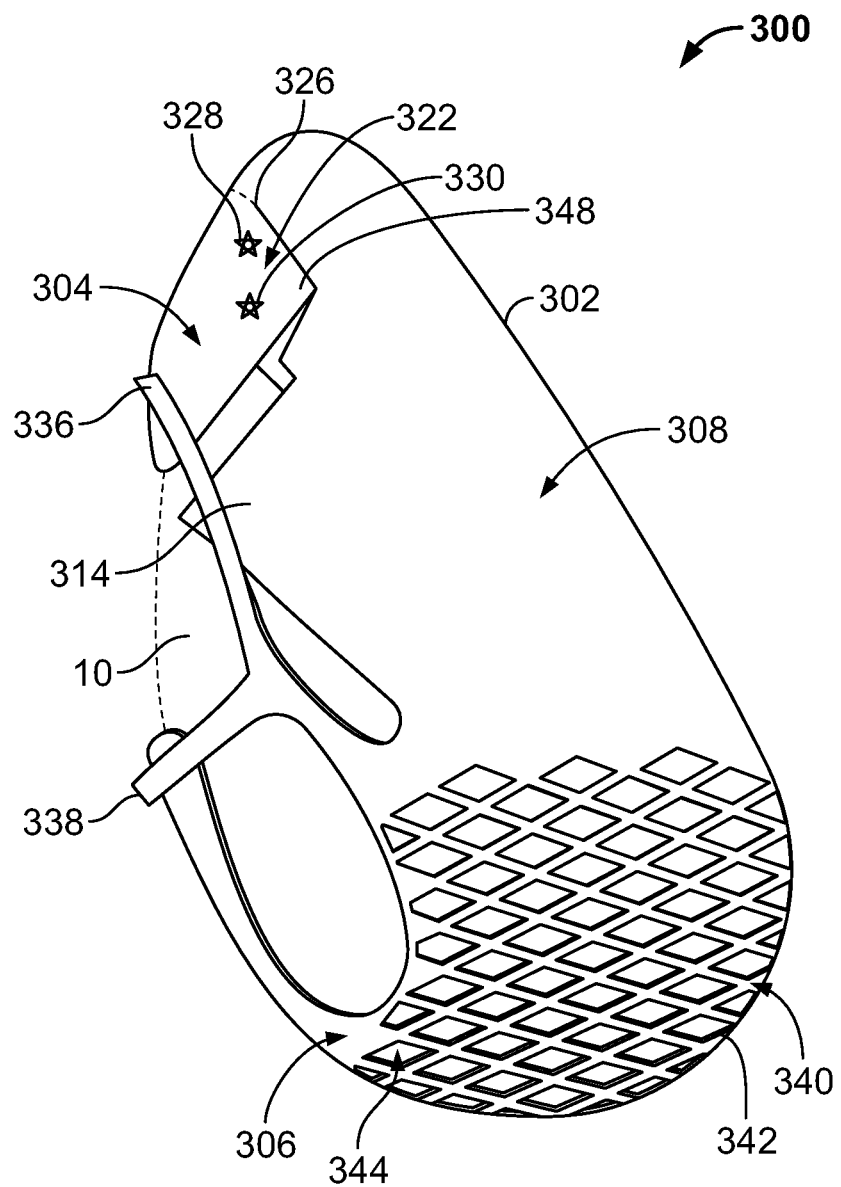
FIG. 12 is a side view of a composition in a wrapped configuration relative to a breast implant or tissue expander, according to certain embodiments.
Figure 13:
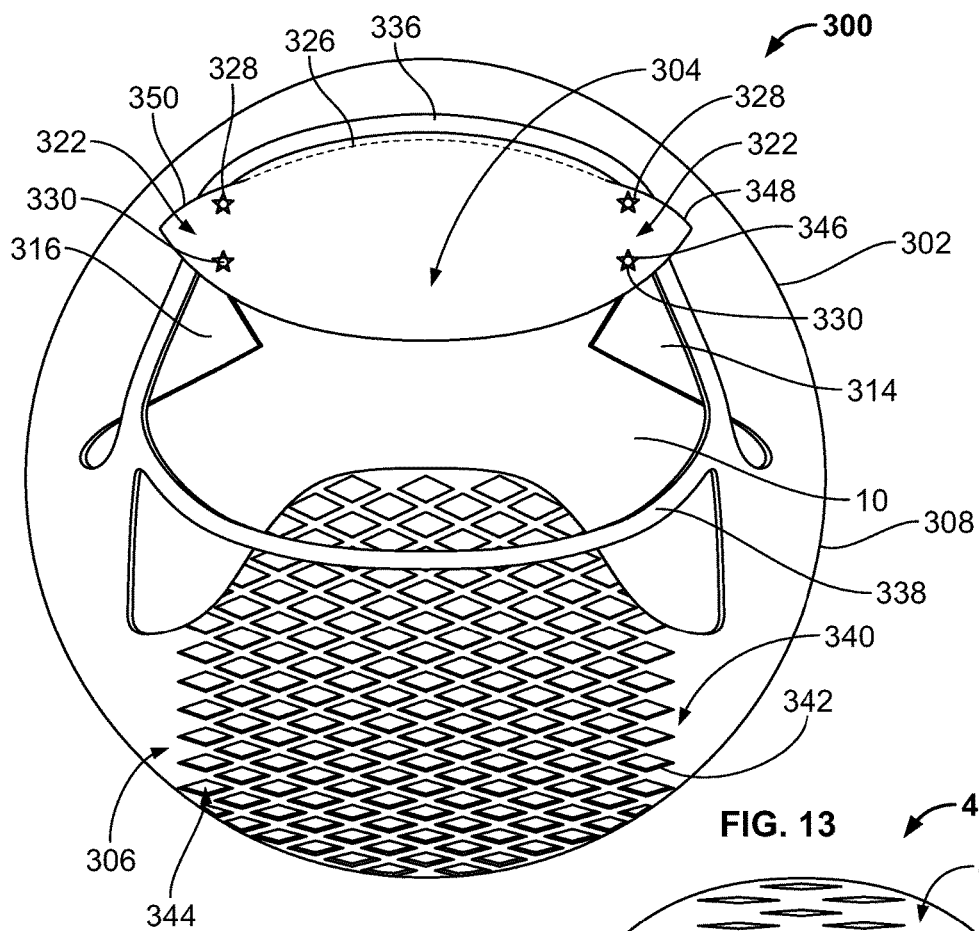
FIG. 13 is a rear view of a composition in a wrapped configuration relative to a breast implant or tissue expander, according to certain embodiments.

With respect to FIGS. 12 and 13, side and rear views of the composition 300 completely or nearly completely wrapped around the implant 10 are shown. Initially, the implant 10 can be positioned on and oriented relative to the composition 300 such that the appropriate sections of the implant 10 that require additional support are positioned adjacent to continuous structure portions of the composition 300. For example, as shown in FIGS. 12 and 13, the lower pole 16 of the implant 10 can be positioned at or near the mesh pattern 340 of the bottom region 306 of the composition 300, while the upper pole 14 of the implant 10 can be positioned at or near the top and central regions 304, 308 of the composition 300 defining the continuous structure. However, it should be understood that the implant 10 can be oriented in other ways relative to the composition 300 and/or the composition 300 can include alternative or additional areas including the mesh pattern 340.

In the initial configuration, the composition 300 can be dimensioned smaller than the surface area of the implant 10. However, as shown in FIGS. 12 and 13, one or more areas of the composition body 302 including the mesh patterns 340 can be expanded and stretched to at least partially wrap the composition 300 around the implant 10. For example, the bottom region 306 of the composition 300 can be expanded and stretched to wrap around the lower pole 16 of the implant 10. The mesh pattern 340 can be expanded and stretched by applying a tensile force on the bottom region 306. The slits 342 that form the mesh pattern 340 can expand due to the tensile force to create a plurality of openings 344 that are dimensioned greater than the slits 342 in the non-expanded configuration. In particular, due to the flexibility of the mesh pattern 340, the expansion and stretching of the mesh pattern 340 can be customized based on the particular implant 10 configuration being used. Thus, less material can be used to completely or nearly completely wrap the composition 300 around a variety of implants 10.

During the wrapping process, the top region 304 can be folded along the fold line 326 to align the respective first pair of apertures 322 with the second pair of apertures 324. In certain embodiments, suture 346 can be passed through the apertures 322, 324 to maintain the top region 304 in the folded configuration. In the folded configuration, the top region 304 can form a first flap 348 and a second flap 350. The first and second flaps 348, 350 can extend outwardly from the surface of the implant 10.

The first and second flaps 314, 316 extending from the central region 308 can be wrapped around portions of the respective right and left sides 20, 22 of the implant 10. The bottom region 306 can be stretched over the lower pole 16 of the implant 10. Thus, in the wrapped configuration, the top region 304, bottom region 306, first flap 314 and second flap 316 can join in a facing, spaced or overlapping manner at the posterior side 28 of the implant 10.

In certain embodiments, to maintain the composition 300 in the wrapped configuration, the first strap 336 can be pulled and stretched upward and disposed around an edge of the top region 304 (e.g., FIG. 12). In certain embodiments, to maintain the composition 300 in the wrapped configuration, the first strap 336 can be pulled and stretched upward and disposed around the first and second flaps 348, 350 of the top region 304 (e.g., FIG. 13). In particular, the first strap 336 can fit between the first and second flaps 348, 350 and the implant 10 and/or the first and second flaps 314, 316 to maintain the first strap 336 interlocked relative to the top region 304. Specifically, the edges of the first and second flaps 348, 350 prevent the first strap 336 from returning to a position adjacent to the bottom region 306. Stretching the first strap 336 from the bottom region 306 to the top region 304 creates tension in the first strap 336, thereby maintaining a tight grip on the first and second flaps 348, 350. The tension in the first strap 336 also maintains the top region 304 wrapped around the implant 10.

Portions of the first strap 336 can pass over the first and second flaps 314, 316, thereby also maintaining the first and second flaps 314, 316 wrapped around the implant 10. The second strap 338 can be stretched and wrapped around a portion of the bottom region 306. The tension in the second strap 338 maintains pressure on the bottom region 306, thereby ensuring that the bottom region 306 remains wrapped around the implant 10. As such, the first and second straps 336, 338 assist in maintaining the composition 300 completely or nearly completely wrapped around the implant 10.

Figure 14:
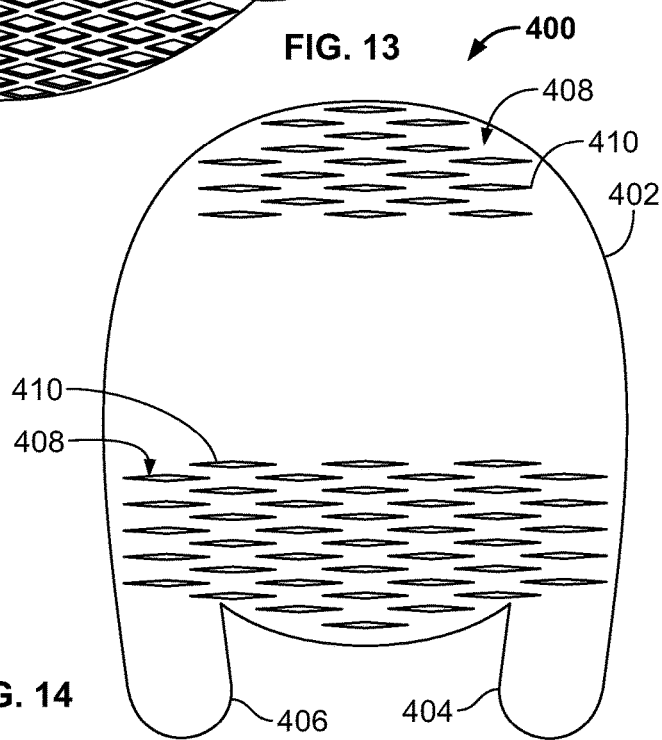
FIG. 14 is a front view of a composition, according to certain embodiments.

With reference to FIG. 14, a front view of another embodiment of an exemplary composition 400 is shown. In certain embodiments, the composition 400 can be made from processed tissue, e.g., an acellular tissue matrix, an acellular dermal matrix, or the like. In certain embodiments, the composition 400 can be made from a synthetic material. In certain embodiments, the composition 400 can be made from a combination of processed tissue and synthetic materials.

The composition 400 includes a composition body 402 formed as a single piece of material. The composition body 402 can be shaped or formed into a substantially flat or sheet-like configuration. However, the composition body 402 can be flexible such that the composition body 402 can conform to or wrap around the three-dimensional shape of the implant 10.

In certain embodiments, the composition body 402 can define, e.g., a rectangular shape, a square shape, an oval shape, a circular shape, or the like. The composition 400 can include two or more tabs or flaps 404, 406 extending from one end of the composition body 402. For example, the flaps 404, 406 can extend from the bottom edge of the composition body 402. In certain embodiments, the composition 400 can include flaps 404, 406 extending from the bottom and/or side edges of the composition body 402.

In certain embodiments, the composition 400 can include one or more mesh patterns 408 formed therein. The mesh patterns 408 can be formed from a plurality of slits 410 formed in and passing through the composition body 402. In certain embodiments, the slits 410 can be formed in a horizontal direction. In certain embodiments, the slits 410 can be formed in a vertical direction. In certain embodiments, adjacent rows of slits 410 can be staggered or offset relative to each other. In certain embodiments, the slits 410 can be linear, angled, a combination thereof, or the like. Each slit 410 can be configured and dimensioned to allow passage of a single flap 404, 406 therethrough. As described above, the mesh patterns 408 allow portions of the composition body 402 to be expanded and stretched to conform the composition body 402 to the three-dimensional shape of the implant 10, thereby allowing the implant 10 to be at least partially wrapped with the composition 400.

Figure 15:
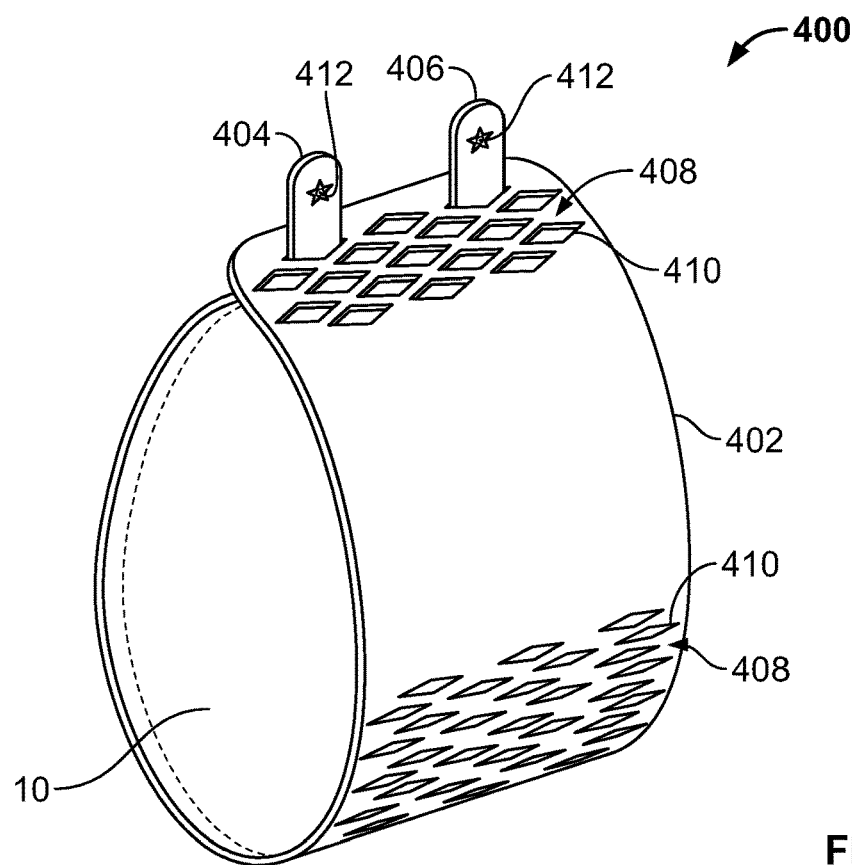
FIG. 15 is a perspective view of a composition in a wrapped configuration relative to a breast implant or tissue expander, according to certain embodiments.

With reference to FIG. 15, a perspective view of the composition 400 completely or nearly completely wrapped around the implant 10 is provided. Initially, the implant 10 can be positioned on or oriented relative to the composition 400 such that the appropriate sections of the implant 10 that require additional support are positioned adjacent to continuous structure portions of the composition 400 (e.g., areas without the mesh pattern 408). In the initial configuration, the composition 400 can be dimensioned smaller than the surface area of the implant 10. However, as shown in FIG. 15, one or more areas of the composition body 402 including the mesh patterns 408 can be expanded and stretched to at least partially wrap the composition 400 around the implant 10. For example, the mesh patterns 408 shown in FIG. 15 can be expanded or stretched to wrap around portions of the upper and lower poles 14, 16 of the implant 10. The mesh pattern 408 can be expanded or stretched by applying a tensile force on the edges of the composition body 402. The slits 410 that form the mesh pattern 408 can expand due to the tensile force to create a plurality of openings that are dimensioned greater than the slits 410 in the non-expanded configuration. In particular, due to the flexibility of the mesh patterns 408, the expansion and stretching of the mesh patterns 408 can be customized based on the particular implant 10 configuration being used. Thus, less material can be used to wrap the composition 400 around a variety of implants 10.

During the wrapping process, the implant 10 can be positioned on and oriented relative to the composition 400. The top and bottom edges of the composition 400 can be wrapped around the implant 10 such that the top and bottom edges meet in a facing relation. As the composition 400 is wrapped around the implant 10, the mesh patterns 408 can expand and stretch to conform the composition 400 to the three-dimensional form of the implant 10. The flaps 404, 406 can be passed through two slits 410 of the mesh pattern 408 near the adjacent edge of the composition body 402.

In certain embodiments, suture 412 can be used to secure the flaps 404, 406 to the composition body 402 such that the flaps 404, 406 cannot pass out of the slits 410. The flaps 404, 406 thereby act as fastening elements and maintain the composition 400 stretched and wrapped around the implant 10. In certain embodiments, the composition 400 can include tabs extending from side edges of the composition 400 such that the sides of the implant 10 can be fully covered by the composition 400 in the wrapped configuration.

Figure 16:
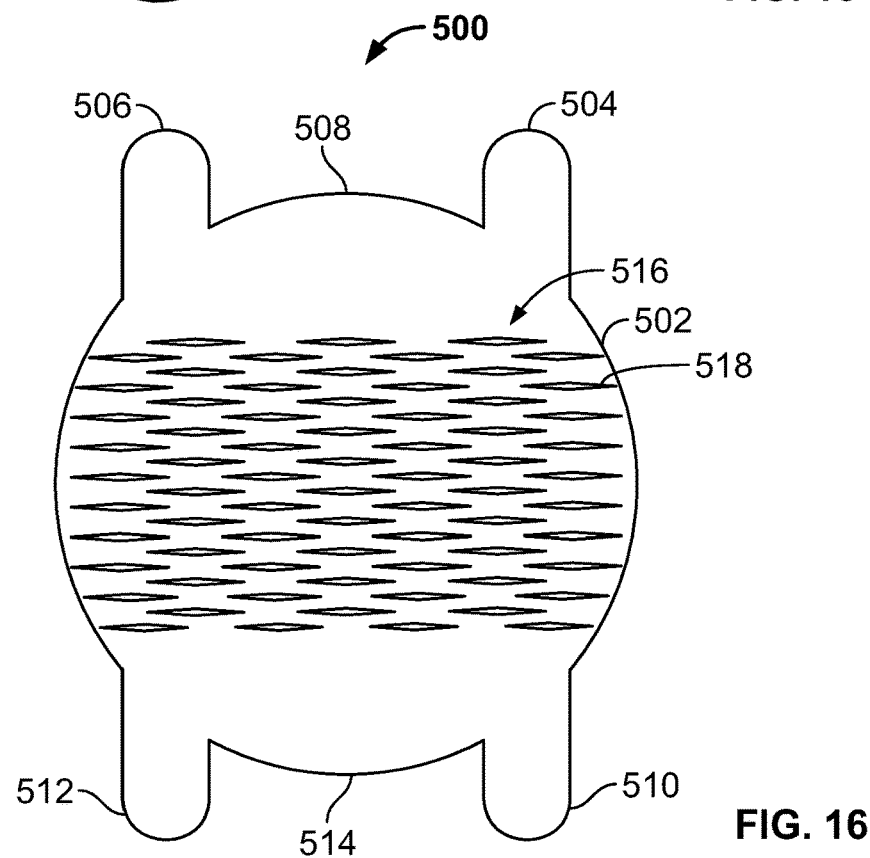
FIG. 16 is a front view of a first composition half, according to certain embodiments.
Figure 17:
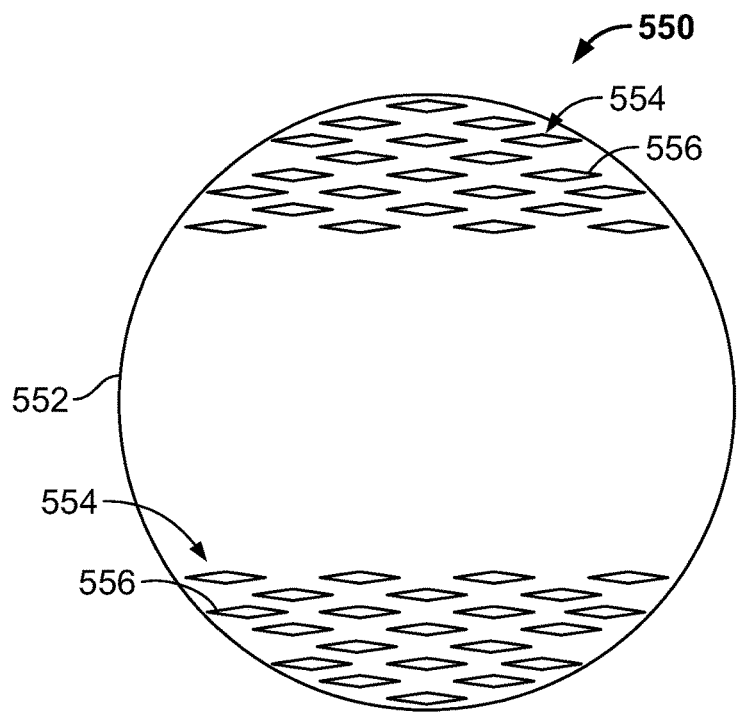
FIG. 17 is a front view of a second composition half, according to certain embodiments.

With reference to FIGS. 16 and 17, front views of another embodiment of an exemplary composition (e.g., first and second composition halves 500, 550) are shown. As will be discussed in greater below, the first and second composition halves 500, 550 can mate relative to each other to at wrap around and at least partially cover the implant 10. In certain embodiments, the composition halves 500, 550 can be made from processed tissue, e.g., an acellular tissue matrix, an acellular dermal matrix, or the like. In certain embodiments, the composition halves 500, 550 can be made from a synthetic material. In certain embodiments, the composition halves 500, 550 can be made from a combination of processed tissue and synthetic materials.

The first composition half 500 includes a composition body 502. The composition body 502 can be shaped or formed into a substantially flat or sheet-like configuration. However, the composition body 502 can be flexible such that the composition body 502 can conform to or wrap around a portion of the three-dimensional shape of the implant 10.

In certain embodiments, the composition body 502 can define, e.g., a rectangular shape, a square shape, an oval shape, a circular shape, or the like. The first composition half 500 can include two or more tabs or flaps 504, 506 extending from a top edge 508 of the composition body 502. The first composition half 500 can include two or more tabs or flaps 510, 512 extending from a bottom edge 514 of the composition body 502. In particular, the flaps 504, 506 can extend in a parallel manner relative to the flaps 510, 512. In certain embodiments, the flaps 504, 506 and the flaps 510, 512, respectively, can extend in line or be aligned relative to each other. In certain embodiments, the flaps 504, 506, 510, 512 can be formed integrally and from the same material as the composition body 502. In certain embodiments, the first composition half 500 can include flaps extending from the side edges of the composition body 502.

In certain embodiments, the first composition half 500 can include one or more mesh patterns 516 formed therein. The mesh patterns 516 can be formed from a plurality of slits 518 formed in and passing through the composition body 502. In certain embodiments, the slits 518 can be formed in a horizontal direction. In certain embodiments, the slits 518 can be formed in a vertical direction. In certain embodiments, adjacent rows of slits 518 can be staggered or offset relative to each other. In certain embodiments, the slits 518 can be linear, angled, a combination thereof, or the like. In certain embodiments, the mesh patterns 516 can be formed in a substantial portion of the composition body 502 (e.g., areas excluding the flaps 504, 506, 510, 512). In certain embodiments, the mesh patterns 516 can be formed in a central portion of the composition body 502 (e.g., leaving portions of the composition body 502 as continuous structures). In certain embodiments, the As described above, the mesh patterns 516 allow portions of the composition body 502 to be expanded and stretched to conform the composition body 502 to the three-dimensional shape of the implant 10, thereby allowing the implant 10 to be at least partially wrapped with the first composition half 500.

The second composition half 550 includes a composition body 552. The composition body 552 can be shaped or formed into a substantially flat or sheet-like configuration. However, the composition body 552 can be flexible such that the composition body 552 can conform to or wrap around a portion of the three-dimensional shape of the implant 10.

In certain embodiments, the composition body 552 can define, e.g., a rectangular shape, a square shape, an oval shape, a circular shape, or the like. In certain embodiments, the composition body 552 can define a shape substantially complementary to the shape of the composition body 502 of the first composition half 500. In certain embodiments, the second composition half 550 can include one or more mesh patterns 554 formed therein. The mesh patterns 554 can be formed from a plurality of slits 556 formed in and passing through the composition body 552. In certain embodiments, the slits 556 can be formed in a horizontal direction. In certain embodiments, the slits 556 can be formed in a vertical direction. In certain embodiments, adjacent rows of slits 556 can be staggered or offset relative to each other. In certain embodiments, the slits 556 can be linear, angled, a combination thereof, or the like. Each slit 556 can be configured and dimensioned to allow passage of a single flap 504, 506, 510, 512 of the first composition half 500 therethrough.

In certain embodiments, the mesh patterns 554 can be formed in a substantial portion of the composition body 552 (e.g., covering the surface area within the edges of the composition body 552). In certain embodiments, the mesh patterns 554 can be formed in a central portion of the composition body 552 (e.g., leaving portions of the composition body 552 as continuous structures). In certain embodiments, the mesh patterns 554 can be formed at the edges of the composition body 552 (e.g., leaving the central area of the composition body 552 as a continuous structure). As described above, the mesh patterns 554 allow portions of the composition body 552 to be expanded and stretched to conform the composition body 552 to the three-dimensional shape of the implant 10, thereby allowing the implant 10 to be at least partially wrapped with the second composition half 550.

Figure 18:
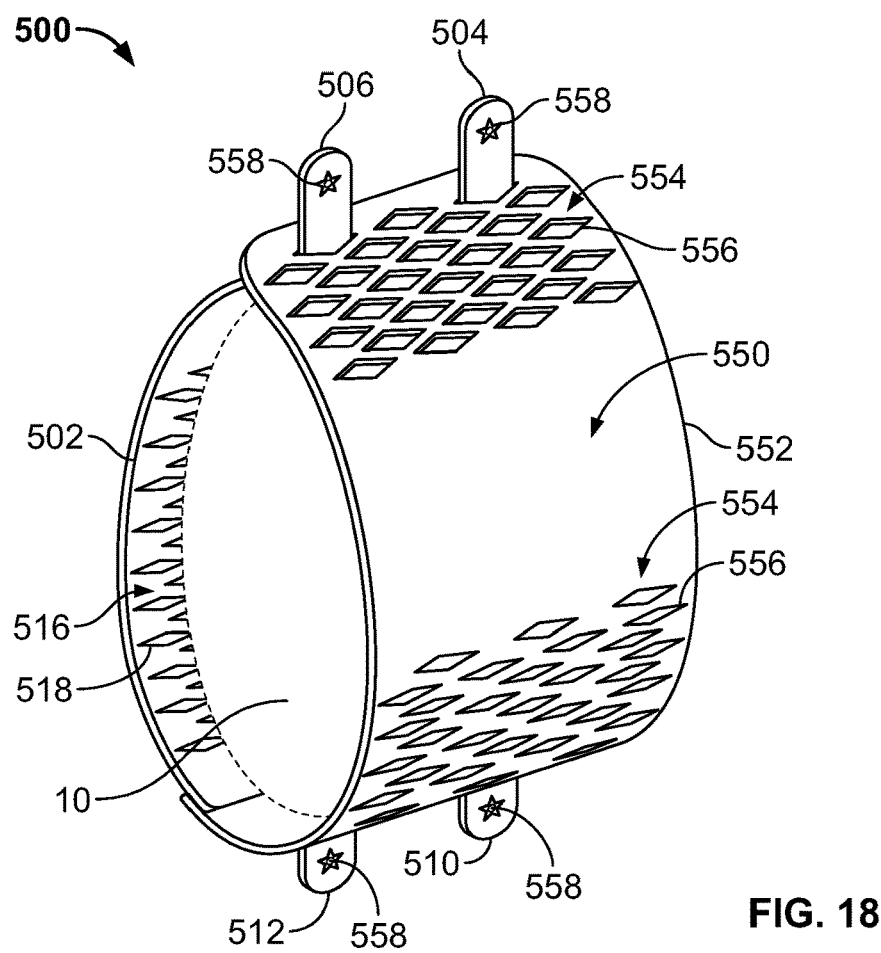
FIG. 18 is a perspective view of a first composition half and a second composition half in a wrapped configuration relative to a breast implant or tissue expander, according to certain embodiments.

With reference to FIG. 18, a perspective view of the first and second composition halves 500, 550 completely or nearly completely wrapped around the implant 10 is provided. For example, the first composition half 500 can wrap around and cover the anterior side 26 of the implant 10, while the second composition half 550 can wrap around and cover the posterior side 28 of the implant 10. Initially, the implant 10 can be positioned on or oriented relative to the first and/or second composition half 500, 550 such that the appropriate sections of the implant 10 that require additional support are positioned adjacent to continuous structure portions of the first and/or second composition half 500, 550 (e.g., areas without the mesh pattern 516, 554).

In the initial configuration, the first and second composition halves 500, 550 can be dimensioned smaller than half of the surface area of the implant 10. However, as shown in FIG. 18, one or more areas of the composition bodies 502, 552 including the mesh patterns 516, 554 can be expanded and stretched to at least partially wrap the first and second composition halves 500, 550 around the implant 10. For example, the mesh pattern 516 of the first composition half 500 can be expanded or stretched to wrap around portions of the posterior side 28 of the implant 10. Similarly, the mesh patterns 554 of the second composition half 550 can be expanded or stretched to wrap around portions of the anterior side 26 of the implant 10.

The mesh patterns 516, 554 can be expanded or stretched by applying a tensile force on the edges of the composition body 502, 552. The slits 518, 556 that form the mesh pattern 516, 554 can expand due to the tensile force to create a plurality of openings that are dimensioned greater than the slits 518, 556 in the non-expanded configuration. In particular, due to the flexibility of the mesh patterns 516, 554, the expansion and stretching of the mesh patterns 516, 554 can be customized based on the particular implant 10 configuration being used. Thus, less material can be used to wrap the first and second composition halves 500, 550 around a variety of implants 10.

During the wrapping process, the implant 10 can be positioned on and orientated relative to the first composition half 500. The top and bottom edges 508, 514 of the first composition half 500 can be wrapped around a portion of the implant 10 (e.g., the posterior side 28) such that the flaps 504, 506 extend over the top side of the implant 10 and the flaps 510, 512 extend over the bottom side of the implant 10. As the first composition half 500 is wrapped around the implant 10, the mesh pattern 516 can expand and stretch to conform the first composition half 500 to the three-dimensional form of one half of the implant 10.

The second composition half 550 can be positioned on and oriented relative to the implant 10. The second composition half 550 can be wrapped around a portion of the implant 10 (e.g., the anterior side 26) such that the top edge of the second composition half 550 is positioned adjacent to the flaps 504, 506 of the first composition half 500, and such that the bottom edge of the second composition half 550 is positioned adjacent to the flaps 510, 512 of the first composition half 500. As the second composition half 550 is wrapped around the implant 10, the mesh patterns 554 can expand and stretch to conform the second composition half 550 to the three-dimensional form of the opposing half of the implant 10. The flaps 504, 506 can be passed through two slits 556 of the mesh pattern 554 near the top edge of the second composition half 550. Similarly, the flaps 510, 512 can be passed through two slits 556 of the mesh pattern 554 near the bottom edge of the second composition half 550.

In certain embodiments, suture 558 can be used to secure the flaps 504, 506, 510, 512 to the composition body 552 such that the flaps 504, 506, 510, 512 cannot pass out of the slits 556. The flaps 504, 506, 510, 512 thereby act as fastening elements and maintain the first and second composition halves 500, 552 stretched and wrapped around the implant 10. In particular, the flaps 504, 506, 510, 512 maintain the first and second halves 500, 550 interlocked relative to each other. In certain embodiments, the first and second composition halves 500, 550 can include flaps extending from side edges such that the sides of the implant 10 can be fully covered by the first and second composition halves 500, 550 in the wrapped configuration.

The compositions described herein can therefore be implemented to cover an implant or tissue expander in an adjustable manner. In particular, the compositions include one or more mesh patterns formed therein that allow for expansion and stretching of the composition body to conform to the three-dimensional shape and size of the implant or tissue expander. Thus, a smaller amount of material can be used to form the compositions, while ensuring that sufficient coverage and support is provided to the implant or tissue expander.

Although the compositions, systems and methods of the present disclosure have been described with reference to exemplary embodiments thereof, the present disclosure is not limited to such exemplary embodiments and or implementations. Rather, the compositions and methods of the present disclosure are susceptible to many implementations and applications, as will be readily apparent to persons skilled in the art from the disclosure hereof. The present disclosure expressly encompasses such modifications, enhancements and or variations of the disclosed embodiments. Since many changes could be made in the above exemplary embodiments and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

What is claimed is:

1. A method of treatment, comprising:
providing a composition, the composition including a tissue matrix or synthetic material defining a composition body, the composition body including a central region and at least two extensions having a mesh pattern formed therein, the at least two extensions protruding from opposing sides of the central region;
positioning the composition onto an implant or a tissue expander with the central region of the composition disposed against an anterior side of the implant or the tissue expander;
stretching and expanding the at least two extensions at the mesh pattern to wrap the composition around the implant or tissue expander such that one extension of the at least two extensions is wrapped in a first direction around the implant or tissue expander and another extension of the at least two extensions is wrapped in an opposing direction to secure the composition to the implant or tissue expander; and
engaging the at least two extensions with each other at a posterior side of the implant or the tissue expander, the posterior side opposing the anterior side of the implant or the tissue expander.

2. The method of claim 1, wherein the tissue matrix is a tissue matrix sheet defining a planar and flexible configuration.

3. The method of claim 1, wherein the tissue matrix is an acellular tissue matrix.

4. The method of claim 1, wherein the composition comprises at least two additional extensions protruding from opposing sides of the central region.

5. The method of claim 4, wherein the at least two additional extensions each comprise a mesh pattern formed therein.

6. The method of claim 1, wherein the central region comprises a mesh pattern formed therein.

7. The method of claim 1, comprising interlocking the at least two extensions of the composition with a fastening element to secure the composition to the implant.

8. The method of claim 7, wherein the fastening element detachably interlocks the at least two extensions of the composition.

9. The method of claim 7, wherein the fastening element includes an elongated body with a proximal end and a distal end, the proximal end including a rounded tip.

10. The method of claim 9, wherein a diameter of the rounded tip is dimensioned greater than a width of the elongated body.

11. The method of claim 9, wherein the rounded tip includes a slit configured to receive therethrough the distal end of the fastening element to interlock the fastening element to the two extensions.

12. The method of claim 1, wherein the at least two extensions extend parallel to each other.

13. The method of claim 1, wherein the central region of the composition is mesh-free.

14. The method of claim 1, wherein:
the composition body includes a horizontal axis passing through the central region, the at least two extensions protruding from the opposing sides of the central region and substantially parallel to the horizontal axis;
the composition body includes a vertical axis passing through the central region; and
the composition body includes two additional extensions protruding from opposing sides of the central region and substantially parallel to the vertical axis.

* * * * *